(12) United States Patent
Wang et al.

(10) Patent No.: US 11,230,553 B2
(45) Date of Patent: Jan. 25, 2022

(54) NANNOCYSTIN PROCESS AND PRODUCTS

(71) Applicant: THE RESEARCH FOUNDATION FOR THE STATE UNIVERSITY OF NEW YORK, Albany, NY (US)

(72) Inventors: Zhang Wang, Albany, NY (US); Jun Huang, Albany, NY (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 853 days.

(21) Appl. No.: 15/590,804

(22) Filed: May 9, 2017

(65) Prior Publication Data
US 2017/0320893 A1    Nov. 9, 2017

Related U.S. Application Data

(60) Provisional application No. 62/333,579, filed on May 9, 2016.

(51) Int. Cl.
| | |
|---|---|
| C07K 7/50 | (2006.01) |
| C07D 498/04 | (2006.01) |
| C07K 1/06 | (2006.01) |
| B01J 23/40 | (2006.01) |
| C07K 5/083 | (2006.01) |

(52) U.S. Cl.
CPC .......... C07D 498/04 (2013.01); B01J 23/40 (2013.01); C07K 1/06 (2013.01); C07K 5/0808 (2013.01)

(58) Field of Classification Search
None
See application file for complete search history.

(56) References Cited

U.S. PATENT DOCUMENTS

| | | | |
|---|---|---|---|
| 8,268,775 B2 * | 9/2012 | Hoffmann | A61P 31/00 514/3.4 |
| 2009/0221520 A1 | 9/2009 | Malpartida Romero | |
| 2011/0030656 A1 | 2/2011 | Pepperine et al. | |

FOREIGN PATENT DOCUMENTS

| | | |
|---|---|---|
| EP | 2173756 B1 | 3/2011 |
| EP | 2379074 B1 | 11/2013 |
| JP | 5470665 B1 | 4/2014 |
| WO | 2010069850 A1 | 6/2010 |

OTHER PUBLICATIONS

Kim (Catalytic Ring Closing Metathesis of Dienynes: Construction of Fused Bicyclic Rings, J. Am. Chem. Soc. 1994, 116, 10801-10802) (Year: 1994).*
C.W. Thornber, Chem SOC, Rev. 9(4), (1979) 563-580, 18 pages (Year: 1979).*

Hoffmann, H., et al.. Discovery, Structure Elucidation, and Biological Characterization of Nannocystin A, a Macrocyclic Myxobacterial Metabolite with Potent Antiproliferative Properties; Angew. Chem. Int. Ed. 2015, vol. 54, pp. 10145-10148.
Krastel, P., et al., Nannocystin A: an Elongation Factor 1 Inhibitor from Myxobacteria with Differential Anti-Cancer Properties, Angew. Chem. Int. Ed. 2015, vol. 127, pp. 1-7.
Nicolaou, K. C., et al., Molecules That Changed the World, 2008, pp. 1-368, Wiley-VCH, Weinheim, Germany.
Dias, Daniel A., et al., A Historical Overview of Natural Products in Drug Discovery, Metabolites 2012, vol. 2, pp. 303-336, Australia.
Szychowski, J, et al.. Natural Products in Medicine: Transformational Outcome of Synthetic Chemistry, J. Med Chem. 2014, vol. 57, pp. 9292-9308, United States.
Gogineni, V, et al.. Role of Marine Natural Products in the Genesis of Antiviral Agents, T. Chem. Rev. 2015, vol. 115, pp. 9655-9706, United States.
Mishra, B. B, et al.. Natural products: An evolving role in future drug discovery, Eur. J. Med. Chem. 2011, vol. 46, pp. 4769-4807, India.
Newman, D. J et al.. Natural Products as Sources of New Drugs from 1981 to 2014, J. Nat. Prod. 2016, vol. 79, pp. 629-661, United States.
Lee, M. D et al., Calicheamicins: Discovery, Structure, Chemistry, and Interaction with DNA, Acc. Chem. Res. 1991, vol. 24, pp. 235-243, United States.
Bross, p. F., et al.. Approval Summary: Gemtuzumab Ozogamicin in Relapsed Acute Myeloid Leukemia, Clin Cancer Res. 2001, vol. 7, pp. 1490-1496, United States.
Heitman, J., et al.. Targets for Cell Cycle Arrest by the Immunosuppressant Rapamycin in Yeast, Science 1991, vol. 253, pp. 905-909, United States.
Foster, K. G., Mammalian Target of Rapamycin (mTOR): Conducting the Cellular Signaling Symphony, J. Biol. Chem. 2010, vol. 285, p. 14071-14077, United States.
Easton, J. B., et al., mTOR and cancer therapy, Oncogene 2006, vol. 25, pp. 6436-6446, United States.
Wang, L., et al., Formal Total Synthesis of N-Methylmaysenine, Org. Lett. 2009,11, pp. 1809-1812, China.
Barluenga, S., et al., Modular Asymmetric Synthesis of Pochonin C, Angew. Chem. Int. Ed. 2004, 43, pp. 3467-3470, Germany.

(Continued)

*Primary Examiner* — Thomas S Heard
(74) *Attorney, Agent, or Firm* — Michael Krenicky; Garrett Smith; Steven A. Wood, Jr.

(57) ABSTRACT

Described herein is a process for the total synthesis of macrolactones and macrolactams of formula I

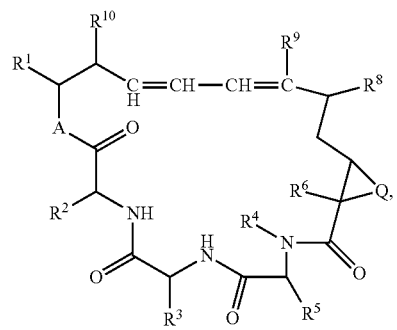

including E- and Z-configuration thereof, in particular, nannocystins.

9 Claims, No Drawings

(56) References Cited

OTHER PUBLICATIONS

Sasikumar, A. N et al., The many roles of the eukaryotic elongation factor 1 complex, WIREs RNA 2012, vol. 3, pp. 543-555, United States.
Dever, T. E., et al., The Elongation, Termination, and Recycling Phases of Translation in Eukaryotes, Cold Spring Harb Perspect Biol 2012, vol. 4, pp. 1-18, United States.
Pecorari, L., Elongation Factor 1 alpha interacts with phospho-Akt in breast cancer cells and regulates their proliferation, survival and motility, Mol. Cancer 2009, vol. 8, No. 58, pp. 1-11, United States.
Lamberti, A., et al.. The translation elongation factor 1A in tumorigenesis, signal transduction and apoptosis: Review article, Amino Acids 2004, vol. 26, pp. 443-448, Austria.
Dua, K., et al., Translational control of the proteome: Relevance to cancer, Proteomics 2001, vol. 1, pp. 1191-1199, United States.
Lee, J. M., The role of protein elongation factor eEF1A2 in ovarian cancer, Reprod. Biol. Endocrinol. 2003,1, No. 69, pp. 1-5, Canada.
Huang, Jun, et al., Total Synthesis of Nannocystin AO, a Potent Elongation Factor 1 Inhibitor, 2016, China.
Gradillas, A., et al., Macrocyclization by Ring-Closing Metathesis in the Total Synthesis of Natural Products Reaction Conditions and Limitations, Angew Chern Int Ed 2006, vol. 45, pp. 6086-6101, United States.
Nicolaou, K. C. et al., Metathesis Reactions in Total Synthesis, Angew. Chern. Int. Ed. 2005, vol. 44, pp. 4490-4527, Germany.
Prunet, J., Progress in Metathesis Through Natural Product Synthesis, Eur. J. Org. Chem. 2011, pp. 3634-3647, Germany.
Hoveyda, A. H., et al.. The remarkable metal-catalysed olefin metathesis reaction, Nature 2007, 450, pp. 243-2510, United States.
Fürstner, A, Metathesis in total synthesis, Chern. Commun., 2011,47, pp. 6505-6511, Germany.
Wang, Y., et al., Synthesis of the Conjugated Tetraene Acid Side Chain of Mycolactone E by Suzuki-Miyaura Cross-Coupling Reaction of Alkenyl Boronates, Eur. J. Org. Chem. 2014, 323-330, Germany.
Jain, P., et al.. Chiral Bronsted Acid-Catalyzed Allylboration of Aldehydes, J. Am. Chem. Soc. 2010, 132, p. 11884-11886.
Xu, J., Nature-Inspired Total Synthesis of (-)-Fusarisetin A, J. Am. Chem. Soc. 2012, 134, pp. 5072-5075.
Luche, J.-L., Lanthanides in Organic Chemistry. 1 .Selectrive 1,2 Reductions of Conjugated Ketones, J. Am. Chem. Soc. 1978, 100, pp. 2226-2227, United States.
Littke, A. F., et al., Pd/P(t-Bu)3: A Mild and General Catalyst for Stille Reactions of Aryl Chlorides and Aryl Bromides, J. Am. Chem. Soc. 2002, 124, pp. 6343-6348, United States.
Han, X., et al., Cuprous Chloride Accelerated Stille Reactions. A General and Effective Coupling System for Sterically Congested Substrates and for Enantioselective Synthesis, J. Am Chem. Soc. 1999, 121, pp. 7600-7605.
Sao, Y., et al., Catalytic Asymmetric Epoxidation and Kinetic Resolution: Modified Procedures Including in Situ Derivatization, J. Am. Chem. Soc. 1987, 109, pp. 5765-5780.
Shibuya, M., et al., 2-Azaadamantane N-Oxyl (AZADO) and 1-Me-AZADO: Highly Efficient Organocatalysts for Oxidation of Alcohols, J. Am. Chem. Soc. 2006, 128, 8412-8413, Japan.
Kuranaga, T., et al., Total Synthesis and Complete Structural Assignment of Yaku'amide A, J. Am. Chem. Soc. 2013, 135, pp. 5467-5474, Japan.
Dettwiler, J. E., et al.. Synthesis and application of L-N-Boc-N-methyl hydroxyvaline in the preparation of a depsipeptide. Can. J Chem. 2005, vol. 83, 793-800, Canada.
Brown, H. C., et al., Chiral Synthesis via Organoboranes. 7. Diastereoselective and Enantioselective Synthesis of erythro- and threo-B-Methylhomoallyl Alcohols via Enantiomeric (Z)- and (E)-Crotylboranes, J. Am. Chem. Soc. 1986, 108, pp. 5919-5923, United States.
Roush, W. R., et al., Asymmetric Synthesis Using Diisopropyl Tartrate Modified (E)- and (Z)-Crotylboronates Preparation of the Chiral Crotylboronates and Reactions with Achiral Aldehydes, J. Am. Chem. Soc. 1990,112, pp. 3339-6348, United States.
Denmark, S. E., et al., Chiral Phosphoramide-Catalyzed Enantioselective Addition of Allylic Trichlorosilanes to Aldehydes. Preparative Studies with Bidentate Phosphorus-Based Amides, J. Org. Chem. 2005, 71, pp. 1523-1536.
Kim, H., et al., A More Comprehensive and Highly Practical Solution to Enantioselective Aldehyde Crotylation, J. Am. Chem. Soc 2011,133, pp. 6517-6520.
Meng, F et al., Cu-Catalyzed Chemoselective Preparation of 2-(Pinacolato)boron-Substituted Allylcopper Complexes and their In Situ Site-, Diastereo-, and Enantioselective Additions to Aldehydes and Ketones, Angew. Chem. Int. Ed. 2013, 52, 5046-5051, Germany.
Humphrey, J. M et al., Chemical Synthesis of Natural Product Peptides: Coupling Methods for the Incorporation of Moncoded Amino Acids into Peptides, Chem. Rev. 1997, 97, pp. 2243-2266, United States.
Prabhu, G., et al., Amino acid chlorides: a journey from instability and racemization toward broader utility in organic synthesis including peptides and their mimetics, Tetrahedron 2015, 71, pp. 2785-2832, India.
Burns, A. R., et al., Total Synthesis and Structural Reassignment of (+)- Dictyosphaeric Acid A: A Tandem ntramolecular Michael Addition/Alkene Migration Approach, Angew. Chem. Int. Ed. 2010, 49, pp. 5574-5584, United Kingdom.
Biswas, K., et al.. Highly Concise Routes to Epothilones: The Total Synthesis and Evaluation of Epothilone 490, J. Am. Chem. Soc 2002, 124, pp. 9825-9832, United States.
Yang, Z.-Q., et al.. New Efficient Synthesis of Resorcinylic Macrolides via Ynolides: Establishment of Cycloproparadicicol as Synthetically Feasible Preclinical Anticancer Agent Based on Hsp90 as the Target, J. Am. Chem. Soc. 2004,126, pp. 7881-7889, United States.
Lu, K., et al.. Development of a Concise and Diversity-Oriented Approach for the Synthesis of Plecomacrolides via the Diene-Ene RCM, Org. Lett. 2006, 8, pp. 1193-1196, China.

\* cited by examiner

NANNOCYSTIN PROCESS AND PRODUCTS

CROSS-REFERENCE TO RELATED APPLICATIONS

This application claims priority to U.S. provisional application 62/333,579 filed May 9, 2016, the contents of which are hereby incorporated by reference in their entirety into the present disclosure.

TECHNICAL FIELD

The current disclosure relates generally to synthesis of macrolactones and macrolactams and in particular to an asymmetric total synthesis of nannocystin A0, from simple starting materials.

BACKGROUND OF THE DISCLOSURE

Natural products serve as a main source of therapeutics because of their unique structures and structural diversity.[1] About one half of current small-molecule drugs on the market are natural products or their synthetic analogs. When new natural products with unprecedented structural features are isolated, scientists often find new mechanisms of action for these natural products in biological systems, which could lead to new drug development, as exemplified by research on calicheamicin and rapamycin.[2]

In June 2015, in searching for new bioactive natural products, Hoffmann, et al. reported a family of cyclodepsipeptides called nannocystins, with potent antiproliferative activities against a number of cancer cell lines at nanomolar concentrations.[3] For example, the IC50's of nannocystin A, (1) against HCT116, PC3, and HL60 are 1.2, 1.0, and 12 nM, respectively. Almost simultaneously, Krastel, et al. also discovered the nannocystins and conducted a more comprehensive investigation.[4] They found that nannocystin A, (1) showed anti-proliferative properties against 472 cancer cell lines at nanomolar concentration range. Moreover, a series of experimental and computational studies by Krastel, et al. strongly suggested that the target protein of nannocystins was the elongation factor 1-α (EF-1α). Elongation factors secure accuracy in the translation process and are important in protein synthesis.[5] Cancer cells tend to overexpress elongation factors to expedite protein production.[6] Therefore, compounds that target elongation factors, such as nannocystins, may serve as lead candidates for anticancer therapy.

Based on the potent biological activity of these compounds and subsequent SAR studies, the need for a synthetic process for the preparation of nannocystins became apparent.

SUMMARY OF THE DISCLOSURE

In one aspect, the present disclosure relates to a compound of formula I.

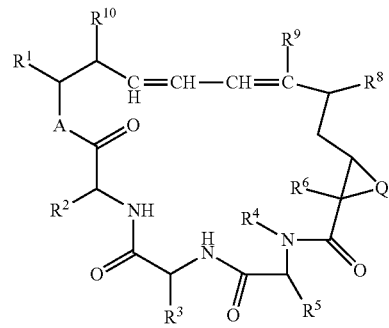

Embodiments include both E- and Z-configurations.

In a related aspect, the present disclosure relates to a process for preparing macrolactones and macrolactams of formula I

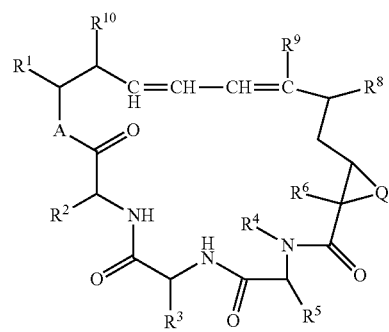

wherein

A is —O— or —NH—;

Q is —O—, —NR$^7$—, or —C(R$^{11}$R$^{12}$)—;

R$^1$ is aryl optionally substituted with one or more substituents chosen independently from —(C$_1$-C$_3$)alkyl, halogen, —(C$_1$-C$_3$)haloalkyl, —(C$_1$-C$_3$)alkyl-OH, and —O(C$_1$-C$_3$)alkyl;

R$^2$ is chosen from hydrogen, (C$_1$-C$_{12}$)hydrocarbyl and —(C$_1$-C$_{12}$)hydrocarbyl-OH;

R$^3$ is phenyl or benzyl optionally substituted with one or more substituents chosen independently from —(C$_1$-C$_3$) alkyl, halogen, —(C$_1$-C$_3$)haloalkyl, —(C$_1$-C$_3$)alkyl-OH, and —O(C$_1$-C$_3$)alkyl;

R$^4$ is hydrogen or (C$_1$-C$_7$)hydrocarbyl;

R$^5$ is hydrogen, (C$_1$-C$_7$)hydrocarbyl or the side chain of a natural amino acid;

R$^6$ is hydrogen or (C$_1$-C$_7$)hydrocarbyl;

R$^7$ is hydrogen or (C$_1$-C$_3$)alkyl;

R$^8$ is chosen from hydrogen, —(C$_1$-C$_3$)alkyl, halogen, hydroxyl, —(C$_1$-C$_3$)haloalkyl, —(C$_1$-C$_3$)alkyl-OH, and —O(C$_1$-C$_3$)alkyl;

R$^9$ is chosen from hydrogen, —(C$_1$-C$_3$)alkyl, halogen, hydroxyl, —(C$_1$-C$_3$)haloalkyl, —(C$_1$-C$_3$)alkyl-OH, —O(C$_1$-C$_3$)alkyl, and —C(O)O(C$_1$-C$_3$)alkyl R$^{10}$ is chosen from hydrogen, (C$_1$-C$_7$)hydrocarbyl and (C$_1$-C$_7$)oxaalkyl;

said process comprising:
reacting a compound of formula II

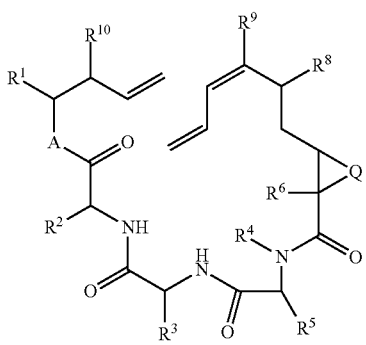

with a ring-closing metathesis catalyst. In one embodiment, the ring-closing metathesis catalyst is a ruthenium catalyst.

In a related aspect, the disclosure relates to a process for preparing a compound of formula II

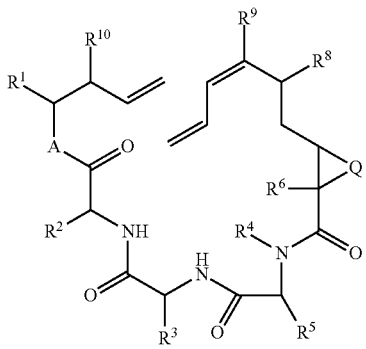

comprising reacting a compound of formula III

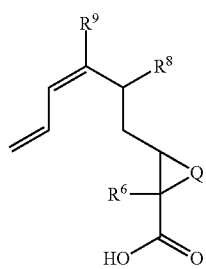

with a compound of formula IV

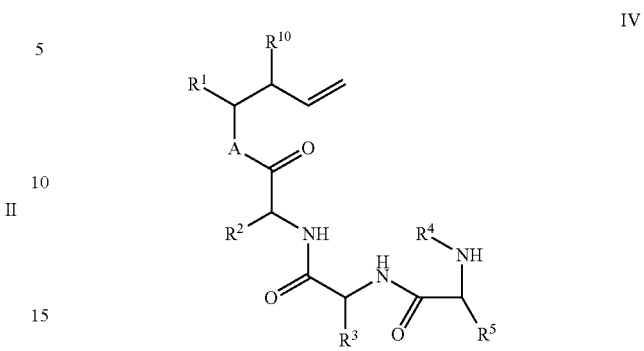

under conditions to form an amide bond.

In another related aspect, the disclosure relates to a process as described above, when $R^4$ is other than hydrogen, conditions include reaction of compound III with 1-chloro-N, N, 2-trimethyl-1-propenylamine followed by reaction with IV in the presence of base.

In yet another related aspect, the disclosure relates to a process wherein, when $R^4$ is hydrogen, conditions include
  (a) reaction of compound III with 1-chloro-N, N, 2-trimethyl-1-propenylamine followed by reaction with IV in the presence of base, or
  (b) reaction of compound III with IV in the presence of a common peptide coupling reagent.

In another aspect, the disclosure relates to a process for preparing a compound of formula III

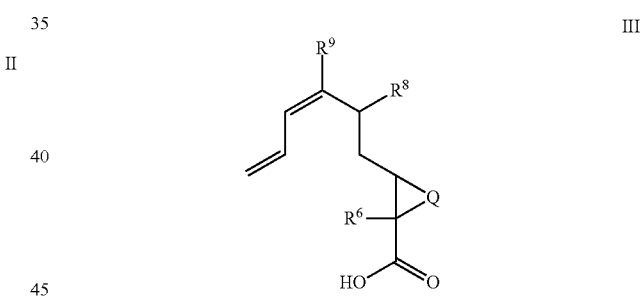

comprising oxidizing a compound of formula V

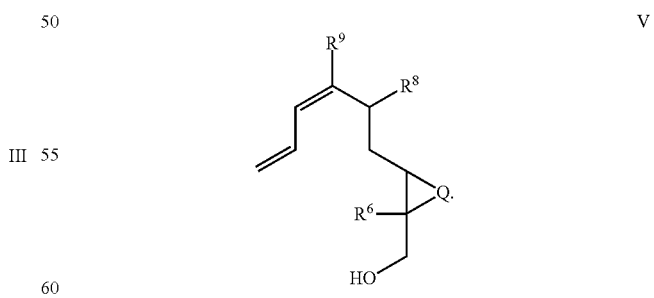

In one embodiment, the oxidation employs as the oxidant trivalent iodine in combination with an n-oxyl. In an embodiment, the process employs diacetoxyiodobenzene and 2-azaadamantane N-oxyl (AZADO) as the oxidant.

In yet another aspect, the disclosure relates to a process for preparing a compound of Formula Va Va

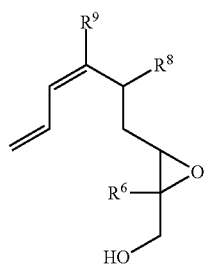

comprising epoxidizing a compound of formula VI

VI

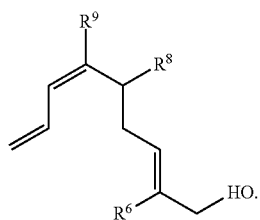

In another aspect, the disclosure relates to a process for preparing a compound of formula VI

VI

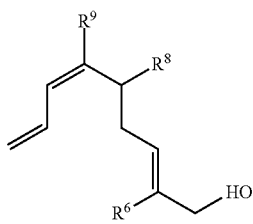

comprising cross coupling of VII

VII

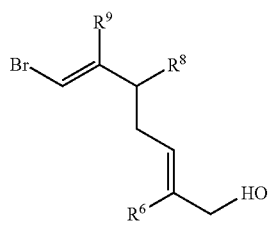

with tributylvinylstannane in the presence of a palladium catalyst.

In another aspect, the disclosure relates to a process for preparing a compound of formula VII

VII

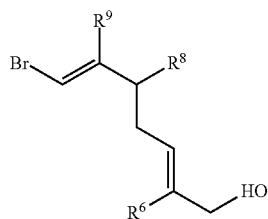

comprising cross metathesis of VIII

VIII

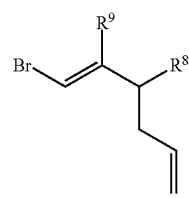

with a methacrolein in the presence of a palladium catalyst, followed by reduction.

In another aspect, the disclosure relates to a process for preparing a compound of formula IV

IV

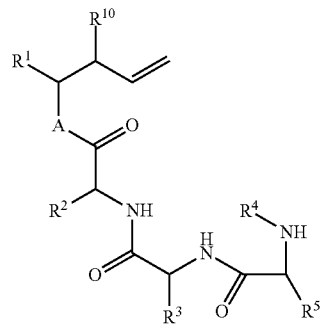

comprising coupling an amine X with a protected acid XI

X

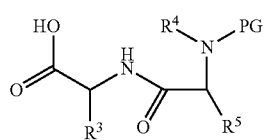

with

XI

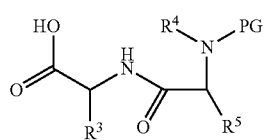

under conditions to form an amide bond and deprotecting, where PG is a protecting group for an amine.

In another aspect, the disclosure relates to a process for preparing an amine of formula Xa Xa

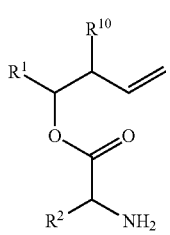

comprising esterification of an alcohol of formula XII

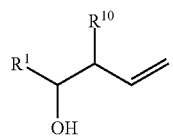

XII with a protected amino acid of formula XIII

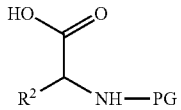

XIII followed by deprotection of the amine.

In another aspect, the disclosure relates to a process according to any one of the above embodiments, wherein the variables, when present, are defined as:
A is —O— or —NH—;
Q is —O— or —CH2-;
R1 is phenyl;
R2 is chosen from hydrogen, methyl, ethyl, propyl, butyl, hydroxymethyl, hydroxypropyl and methylthiomethyl;
R3 is chosen from benzyl, hydroxybenzyl, aminobenzyl, and hydroxybenzyl substituted with one or more halogen;
R4 is hydrogen or methyl;
R5 is hydrogen, propyl, or butyl;
R6 is methyl;
R8 is chosen from hydrogen, hydroxyl, and methoxy;
R9 is chosen from hydrogen and methyl; and
R10 is chosen from hydrogen, methyl, benzyl and cyclopropyl. In one embodiment
A is —O—;
Q is —O—;
R1 is phenyl;
R2 is 2-hydroxy-2-propyl;
R3 is chosen from benzyl, hydroxybenzyl, and hydroxybenzyl substituted with one or more halogen;
R4 is methyl;
R5 is propyl, or butyl;
R6 is methyl;
R8 is methoxy;
R9 is methyl; and
R10 is methyl.

In another aspect, the disclosure relates to a process as described above for preparing macrolactones and macrolactams having the relative stereochemistry shown in formula Ia

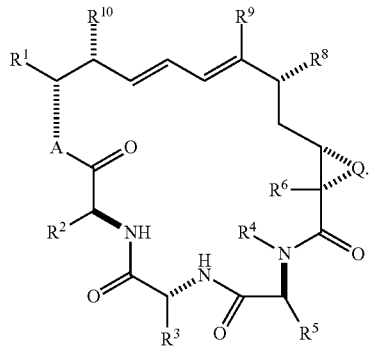

Ia

In another aspect, the disclosure relates to a process as described above for preparing macrolactones and macrolactams having the absolute stereochemistry shown in formula Ib.

DETAILED DESCRIPTION OF THE DISCLOSURE

All patents, publications, applications and other references cited herein are hereby incorporated in their entirety into the present application.

Natural nannocystins (1-9) and their synthetic analogs (10 and 11) are shown in Table 1. Structural features include a 21-membered ring system, 9 chiral centers, two double bonds and a polyketide part with an α, β-epoxy-amide substructure. The ring system consists of a tripeptide part, containing the amino acids 3-hydroxy-valine, 3, 5-dichloro-tyrosine and N-methyl-isoleucine.

TABLE 1

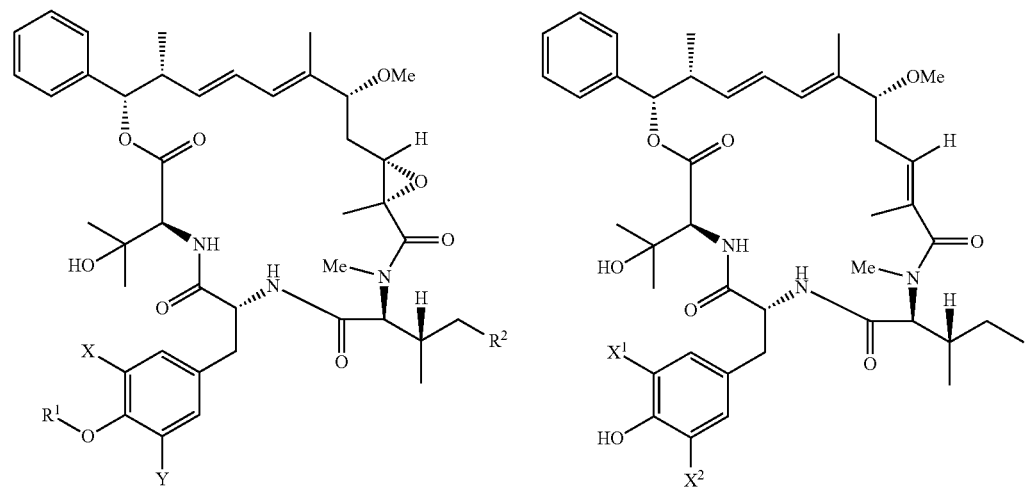

| nannocystins | X | Y | R¹ | R² |
|---|---|---|---|---|
| nannocystin A, 1 | Cl | Cl | H | Me |
| nannocystin A1, 2 | H | Cl | H | Me |

TABLE 1-continued

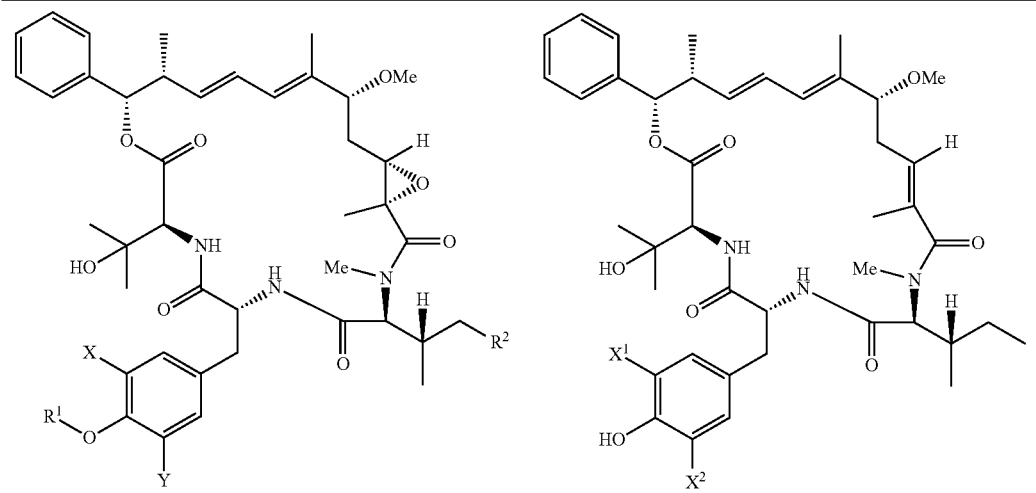

| nannocystins | X | Y | R[1] | R[2] |
|---|---|---|---|---|
| nannocystin A0, 3 | H | H | H | Me |
| nannocystin B, 4 | Cl | Cl | H | H |
| nannocystin B1, 5 | H | Cl | H | H |
| nannocystin A2, 6 | Cl | Br | H | Me |
| nannocystin A3, 7 | Br | H | H | Me |
| nannocystin Ax, 8 | $X_1$ = Cl, | | $X_2$ = Cl | |
| nannocystin Ay, 9 | $X_1$ = Br, | | $X_2$ = H | |
| nannocystin D1, 10 | Cl | Cl | Me | Me |
| nannocystin D2, 11 | Cl | Cl | —(CH$_2$)$_2$NH$_2$ | Me |

The present disclosure describes a convergent synthesis of nannocystins that takes advantage of the ring-closing metathesis (RCM) reaction to assemble the macrocycle. The RCM strategy for macrocycle synthesis is a robust method.[8] Disconnection of the tertiary amide bond of 12 leads to peptide fragment 13 and polyketide motif 14 with approximately equal complexity. Compound 13 is derived from ester 15 through a peptide coupling reaction, and ester 15 is easily prepared from homoallylic alcohol 16. On the other hand, the carboxylic acid 14 can be made via an asymmetric epoxidation of alcohol 17 followed by oxidation. Allylic alcohol 17 can be made via regioselective cross metathesis reaction of a simple compound 18, the asymmetric allylation product of (E)-3-bromomethacrolein.

Scheme 1. Nannocystin A0 Synthesis

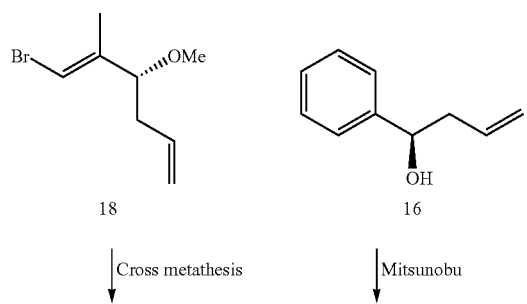

-continued
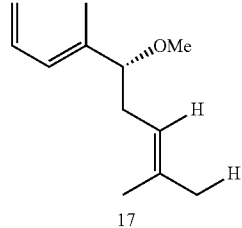
17
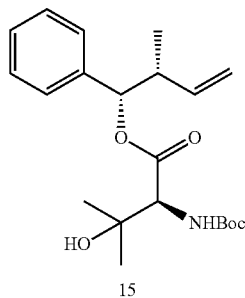
15
↓ Sharpless AE
↓ peptide coupling
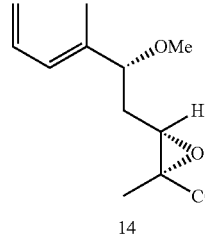
14
+
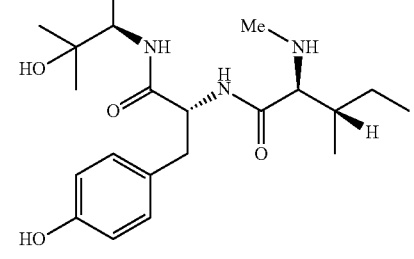
13
↓ Peptide coupling
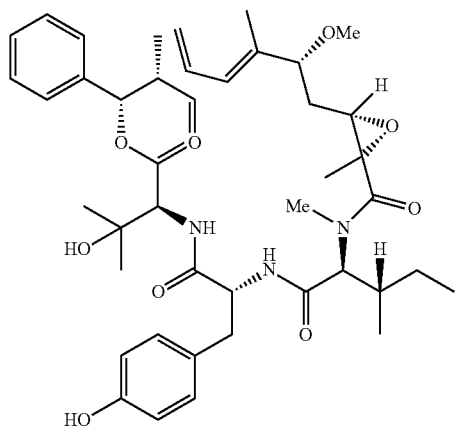
12
↓ RCM

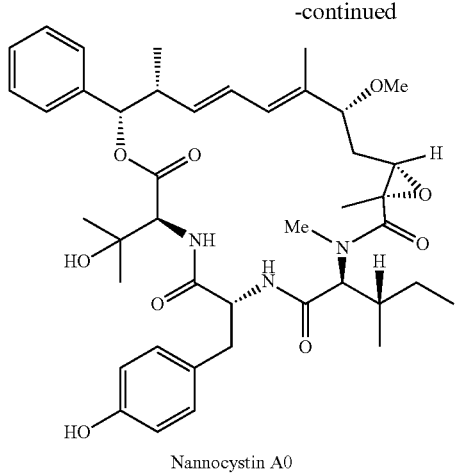
Nannocystin A0
3
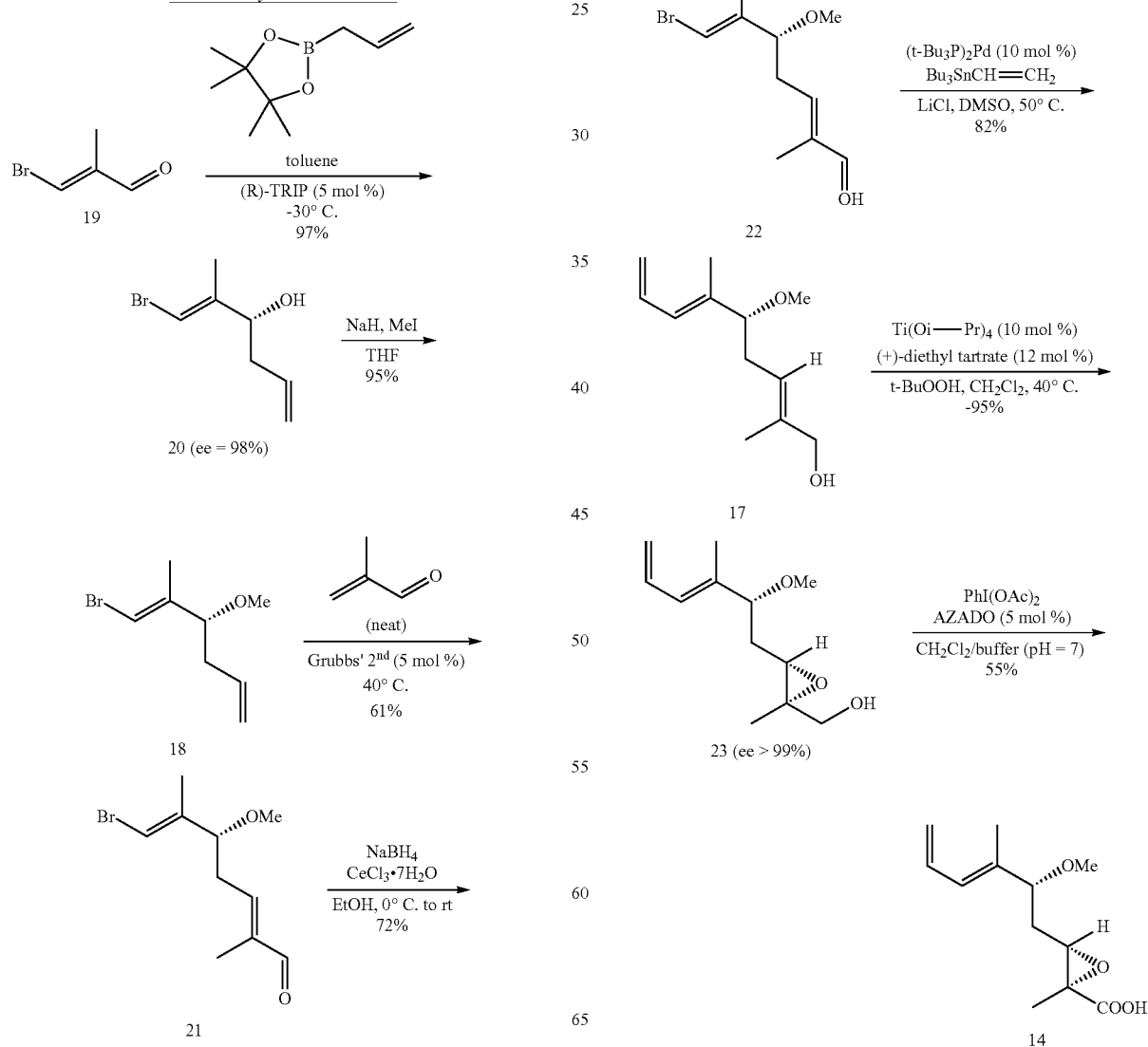
Scheme 2. Synthesis of Acid 14

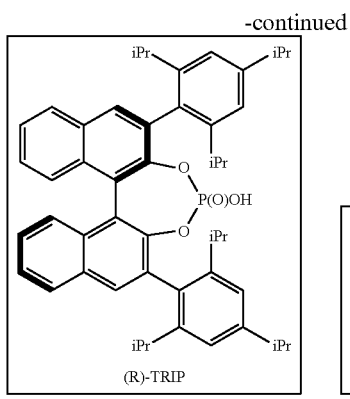

The synthesis of acid 14 started from the known compound (E)-3-bromomethacrolein 19 (Scheme 2).[9] Enantioselective allylation of 19 using Antilla's method provided alcohol 20 in 97% yield with 98% ee.[10] The optical purity of 20 was determined by its UV-active derivative 17 (vide infra). The free hydroxyl group in 20 was methylated by treatment with sodium hydride and iodomethane in 95% yield. Methyl ether 18 underwent cross metathesis with the mono-substituted olefin regio- and stereoselectively using Grubbs' 2nd generation catalyst and neat methacrolein as the solvent,[11] furnishing enal 21 in 61% yield. Prolonged reaction time (36 h) and excess methacrolein is necessary to obtain a good yield of 21 in this step. Luche reduction of enal 21 in ethanol smoothly rendered allylic alcohol 22 in 72% yield.[12] The next goal was to introduce the diene functionality via cross coupling reactions. We found the more active palladium catalyst, Pd(Pt-Bu$_3$)$_2$, to be superior to Pd(PPh$_3$)$_4$ in the Stille coupling reaction with tri-n-butylvinylstannane, furnishing diene 17 in 82% yield.[13] Sharpless asymmetric epoxidation of allylic alcohol 17 gave the desired epoxide 23 in 95% yield with amplified optical purity (>99% ee).[14] Finally, direct oxidation of alcohol 23 to acid 14 using iodosobenzene diacetate and a catalytic amount of 2-azaadamantane-N-oxyl (AZADO) successfully furnished acid 14 in 55% yield.[15]

Scheme 3: Synthesis of Peptide Motif 13

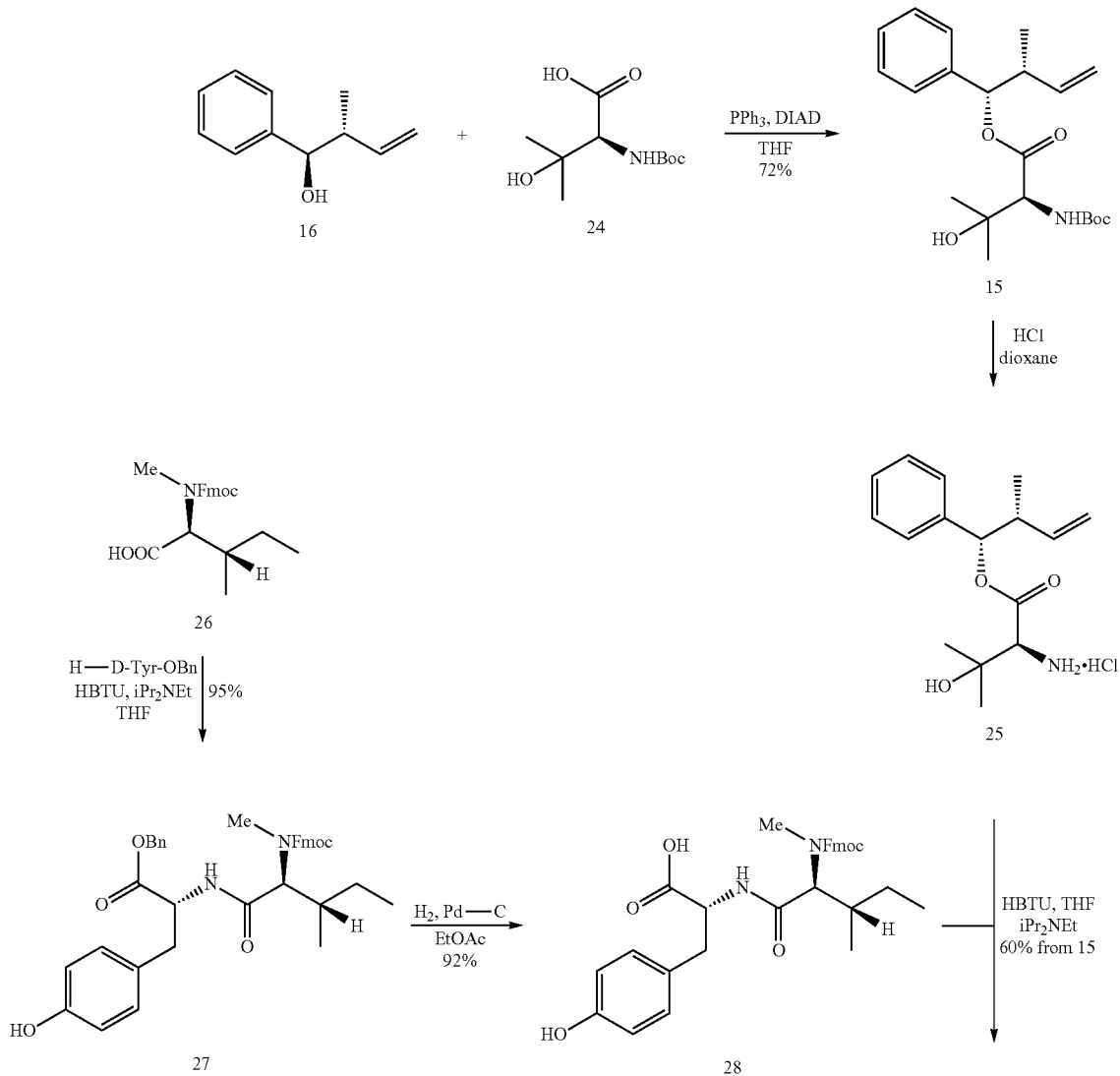

17

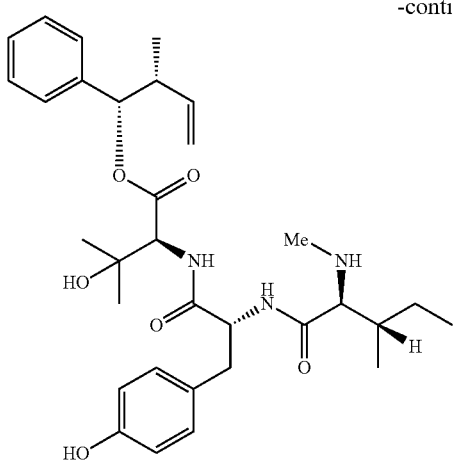

-continued

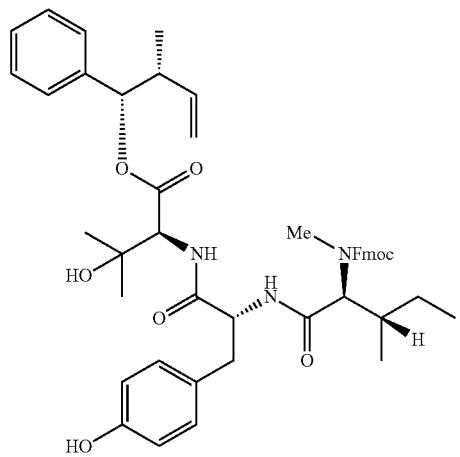

18

The assembly of the peptide motif 13 started from the synthesis of 15 via Mitsunobu reaction between the known free secondary amine 13 was produced after 29 was treated with diethylamine in dry acetonitrile.

Scheme 4. Total Synthesis of Nannocystin A0

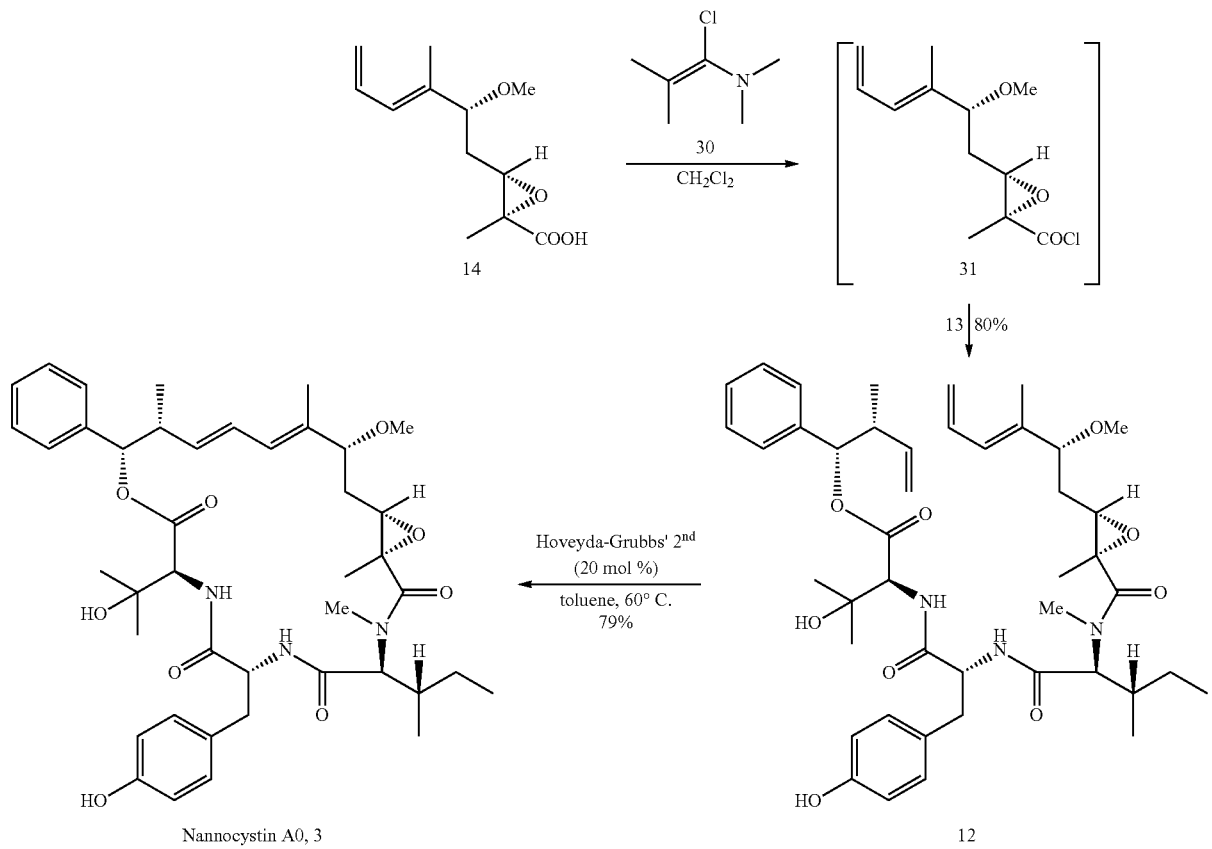

compounds 16 and 24.[16,17] Deprotection of t-butyl carbamate 15 furnished the ammonium salt 25. N-Fmoc-protected N-methyl-L-isoleucine 26 coupled with D-tyrosine benzyl ester successfully, affording dipeptide 27 in 95% yield. After hydrogenolysis of the benzyl group, acid 28 was connected with 25 using HBTU, giving tripeptide 29 in 60% yield. The With fragments 13 and 14 in hand, we turned our attention to the coupling of both termini of 13 and 14 to finish the total synthesis. The carbonyl group in acid 14 is quite hindered due to the tetrasubstituted α-carbon. At the same time, isoleucine is a hindered amino acid in peptide coupling, especially when the nitrogen atom is alkylated.[18] Common peptide coupling reagents such as HATU, HBTU, EDCI, etc., failed to generate the coupled product 12. Focusing on stronger acyl donors generated from 14, it was possible to make the corresponding acyl chloride 31 using Ghosez reagent 30.[19] Crude 31 in a dichloromethane solution was added dropwise into 13 in dichloromethane at −20° C., and desired product 12 was obtained in 80% yield.[20] It should be noted that compounds 29, 13, and 14 should be purified by preparative TLC to remove small amounts of impurities. In addition, compounds 14 and 31 are not very stable, probably due to the acid-sensitive diene moiety, and should be used immediately after preparation. Finally, the target natural product nannocystin A0, 3 was synthesized successfully via ring-closing metathesis of 12 using Hoveyda-Grubbs' 2nd generation catalyst in 79% yield as a 4.6:1 ratio of isomers (3 is the major).[21] The functional group compatibility of this metathesis macrocyclization step is quite remarkable. Pure nannocystin A0, 3 was obtained after separation by reverse-phase HPLC. The NMR spectra of synthetic nannocystin A0 (3) were identical to those of natural nannocystin A0 reported by Krastel, et. al.

The synthetic sequence of nannocystin A0, 3 can be generalized to the synthesis of other nannocystins. We have demonstrated that, starting from 3,5-dichloro-D-tyrosine benzyl ester,[22] nannocystin A, 1 was prepared in the same manner (Scheme 5). The NMR spectra of synthetic nannocystin A, 1 also matched that of natural nannocystin A reported by Krastel.[4]

Convergent total syntheses of nannocystins A and A0 were achieved in nine steps (longest linear sequence) from a simple starting material (E)-3-bromomethacrolein. Noteworthy steps include the peptide coupling with a reactive acyl chloride and a hindered N-methyl-L-isoleucine moiety and the ring-closing metathesis macrocyclization. Our synthetic route will benefit, inter alia, future structure-activity relationship studies of nannocystins.

All reactions were carried out under an argon atmosphere with dry solvents under anhydrous conditions, unless otherwise stated. All chemicals were purchased commercially, and used without further purification. Anhydrous toluene, dichloromethane, tetrahydrofuran, dimethyl sulfoxide, acetonitrile, diethyl ether, 1,4-dioxane for reaction were purchased from EMD Millipore Corporation and used without further purification. Flash chromatography was performed using 230-400 mesh Silia Flash 60® silica gel (Silicycle Inc.). All commercially available amino acid building blocks were purchased from Chem-Impex International, Inc. or Sigma-Aldrich. Other commonly used reagents were purchased from Acros, Alfa-Aesar, Sigma-Aldrich, and used as received without further treatment. Reactions were monitored by thin-layer chromatography (TLC) carried out on 0.25 mm silica gel plates (60F-254) using UV light as visualizing agent and an ethanolic solution of phosphomolybdic acid and cerium sulfate, or an aqueous solution of potassium permanganate and sodium carbonate, and heat as visualizing agents. Organic solutions were concentrated under reduced pressure on a Büchi rotary evaporator. Yields refer to chromatographically purified compounds, unless otherwise stated.

NMR spectra were recorded on either a Bruker Avance 400 ($^1$H: 400 MHz, $^{13}$C: 100 MHz), a Bruker Avance III 400 ($^1$H: 400 MHz, $^{13}$C: 100 MHz), a Bruker Avance III 500 ($^1$H: 500 MHz, $^{13}$C: 125 MHz) or a Bruker Avance III HD600 ($^1$H: 600 MHz, $^{13}$C:150 MHz), and were internally referenced based on solvent peaks (for CDCl$_3$, referenced as 7.26 ($^1$H) and 77.0 ppm ($^{13}$C); as 3.31 ($^1$H) and 49.0 ppm ($^{13}$C) for CD$_3$OD; and as 2.50 ($^1$H) and 39.5 ppm ($^{13}$C) for d$_6$-DMSO). High-resolution mass spectrometric data were obtained using Agilent Technologies 6530 Accurate-Mass Q-TOF LC/MS. Infrared spectra were recorded using a Perkin-Elmer Spectrum Two IR spectrometer. Optical rotations were measured on a Perkin-Elmer 351 polarimeter at 589 nm with a 100 mm path length cell at 25° C. (reported as follows: concentration (c in g/100 mL), solvent). The following abbreviations were used to explain the multiplicities: s=singlet, d=doublet, t=triplet, q=quartet, m=multiplet, b=broad. HPLC analyses were carried out on an Agilent 1100 Series system using a CHIRALCEL OD-H column (4.6×250 mm, 5 micron) with a guard column (4×10 mm, 5 micron). Semi-prep-HPLC was carried out on an Agilent 1100 Series system using a Gemini 5 u C18 110A column (150×10.00 mm, 5 micron).

Additional features of the present disclosure will become apparent to those skilled in the art upon consideration of the following description of illustrative embodiments for carrying out the process.

EXAMPLES

Example 1. Experimental Procedures and Characterization for the Total Synthesis of Nannocystin A and A0

Synthesis of (R,E)-1-bromo-2-methylhexa-1,5-dien-3-ol (20)

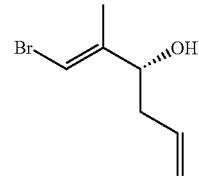

20

A 50 mL flask with a stirring bar was evacuated, flame-dried, and back-filled with argon. To this flask was added the (R)-TRIP catalyst (50 mg, 0.068 mmol), freshly distilled aldehyde 19 (200 mg, 1.35 mmol) and 20 mL of dry toluene. The reaction mixture was then cooled to −30° C. followed by the addition of allyl boronic acid pinacol ester (273 mg, 1.62 mmol) dropwise over 30 seconds. The mixture was stirred overnight at −30° C. and then directly loaded on a silica gel column. The crude product was purified by flash column chromatography on silica gel (hexane/ether=10/1) to give 20 (250 mg) in 97% yield as a colorless oil. 20: $R_f$=0.55 (hexane/ethyl acetate=4/1). $^1$H NMR (400 MHz, CDCl$_3$): δ 6.27 (dd, J=2.3 Hz, 1.1 Hz, 1H), 5.82-5.67 (m, 1H), 5.22-5.16 (m, 1H), 5.14 (t, J=1.1 Hz, 1H), 4.20-4.12 (m, 1H), 2.41-2.29 (m, 2H), 1.80 (d, J=1.2 Hz, 4H). $^{13}$C NMR (100 MHz, CDCl$_3$): δ 142.9, 133.6, 118.7, 104.8, 74.7, 39.7, 15.3. IR (film): ν$_{max}$ 3352, 2917, 1631, 1432, 1288, 1045, 990 cm$^{-1}$; [α]$^{25}_D$=−11.0 (c=0.55, MeOH); HR-MS (m/z): [M+Na]$^+$ calcd for C$_7$H$_{11}$OBrNa$^+$212.9885, found 212.9880.

Synthesis of (R,E)-1-bromo-3-methoxy-2-methyl-hexa-1,5-diene (18)

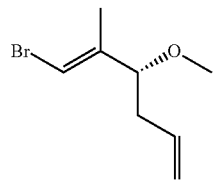

18

To a solution of 20 (135 mg, 0.71 mmol) in dry THF (4 mL) was added MeI (1.01 g, 7.1 mmol) at 0° C. To this solution was added NaH (51 mg, 2.13 mmol) at 0° C., and the mixture was warmed to room temperature, and stirred for 3 h. The reaction mixture was quenched by addition of a saturated aqueous NH$_4$Cl (4 mL), and the mixture was extracted with ether (3×4 mL), and the combined organic layer was washed with brine (2 mL), and dried over Na$_2$SO$_4$. The solvent was removed in vacuo, and the residue was purified by flash column chromatography on silica gel (hexane/ether=100/1) to give 18 (138 mg) in 95% yield as a colorless oil. 18: R$_f$=0.90 (hexane/ethyl acetate=4/1). $^1$H NMR (400 MHz, CDCl$_3$): δ 6.16 (d, J=0.8 Hz, 1H), 5.77-5.56 (m, 1H), 5.15-4.92 (m, 2H), 3.61 (t, J=6.8 Hz, 1H), 3.20 (s, 3H), 2.46-2.31 (m, 1H), 2.31-2.13 (m, 1H), 1.72 (dd, J=4.7, 1.4 Hz, 3H). $^{13}$C NMR (100 MHz, CDCl$_3$): δ 141.1, 134.0, 117.1, 105.3, 84.9, 56.3, 38.1, 14.0. IR (film): ν$_{max}$ 2980, 2933, 2822, 1630, 1449, 1287, 1094, 915 cm$^{-1}$. [α]$^{25}_D$=-1.0 (c=0.25, MeOH). HR-MS (m/z): [M+Na]$^+$ calcd for C$_8$H$_{13}$OBrNa$^+$ 227.0042, found 227.0040.

Synthesis of (R,2E,6E)-7-bromo-5-methoxy-2,6-dimethylhepta-2,6-dienal (21)

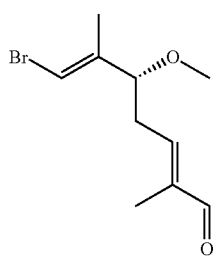

21

To a solution of 18 (1.20 g, 5.88 mmol) in methacrolein (4.86 mL, 58.8 mmol) was added Grubbs catalyst (2$^{nd}$ generation, 250 mg, 0.29 mmol) at room temperature. The reaction mixture was warmed to 40° C., and stirred for 36 hours under argon atmosphere at that temperature. The reaction was allowed to cool to room temperature and concentrated, and the residue was purified by flash column chromatography on silica gel (hexane/ethyl acetate=20/1) to give 21 (883 mg) in 61% yield as a pale yellow oil. 21: R$_f$=0.36 (silica gel, hexanes/ethyl acetate=4/1). $^1$H NMR (400 MHz, CDCl$_3$): δ 9.41 (s, 1H), 6.45 (t, J=7.0 Hz, 1H), 6.24 (s, 1H), 3.80-3.66 (m, 1H), 3.23 (s, 3H), 2.73-2.58 (m, 1H), 2.58-2.34 (m, 1H), 1.76 (s, 3H), 1.74 (s, 3H). $^{13}$C NMR (100 MHz, CDCl$_3$): δ 194.9, 149.0, 140.8, 140.6, 106.0, 83.6, 56.5, 33.4, 14.1, 9.4. IR (film): ν$_{max}$ 2985, 2928, 2823, 1684, 1645, 1440, 1290, 1099 cm$^{-1}$. [α]$^{25}_D$=+5.0 (c=0.9, MeOH). HR-MS (m/z): [M+Na]$^+$ calcd for C$_{10}$H$_{15}$O$_2$BrNa$^+$ 269.0148, found 269.0167.

Synthesis of (R,2E,6E)-7-bromo-5-methoxy-2,6-dimethylhepta-2,6-dien-1-ol (22)

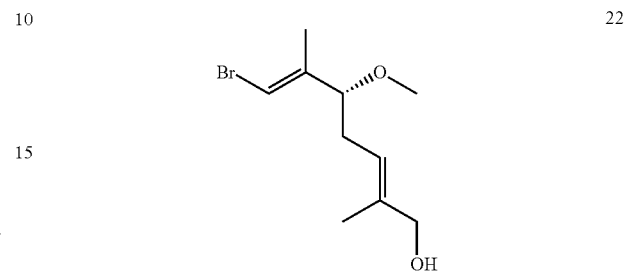

To a stirred solution of 21 (740 mg, 3.01 mmol) in EtOH (20 mL) at 0° C. was added CeCl$_3$.7H$_2$O (1.22 g, 3.30 mmol). After 10 min, NaBH$_4$ (125 mg, 3.30 mmol) was added in one portion. The reaction mixture was allowed to warm to room temperature and stirred for 1 h. Then the reaction mixture was quenched by addition of a saturated aqueous NH$_4$Cl (10 mL), and the mixture was extracted with DCM (4×20 mL), and the combined organic layer was washed with brine (5 mL), and dried over Na$_2$SO$_4$. The solvent was removed in vacuo, and the residue was purified by flash column chromatography on silica gel (hexane/ethyl acetate=8/1) to give 22 (537 mg) in 72% yield as a colorless oil. 22: R$_f$=0.50 (hexane/ethyl acetate=2/1). $^1$H NMR (400 MHz, CDCl$_3$): δ 6.14 (d, J=0.6 Hz, 1H), 5.39-5.21 (m, 1H), 3.98 (s, 2H), 3.58 (t, J=6.9 Hz, 1H), 3.19 (s, 3H), 2.41-2.30 (m, 1H), 2.28-2.17 (m, 1H), 1.74 (s, 1H), 1.72 (d, J=1.1 Hz, 3H), 1.64 (s, 3H). $^{13}$C NMR (100 MHz, CDCl$_3$): δ 141.2, 137.1, 120.7, 105.2, 84.9, 68.5, 56.3, 32.0, 14.0, 13.9. IR (film): ν$_{max}$ 3378, 2924, 2855, 1630, 1438, 1378, 1288, 1092, 1011 cm$^{-1}$. [α]$^{25}_D$=+2.0 (c=0.5, MeOH). HR-MS (m/z): [M+Na]$^+$ calcd for C$_{10}$H$_{17}$O$_2$BrNa$^+$ 271.0304, found 271.0302.

Synthesis of (R,2E,6E)-5-methoxy-2,6-dimethyl-nona-2,6,8-trien-1-ol (17)

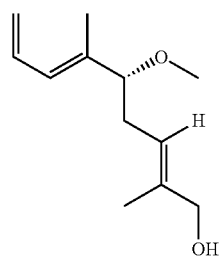

17

A Schlenk tube (50 mL) was charged with LiCl (1.20 g, 28.20 mmol) and flame-dried under high vacuum. Upon cooling, (t-Bu$_3$P)$_2$Pd (144 mg, 0.28 mmol) was added, and the mixture was degassed four times under high vacuum with an argon purge. DMSO (10 mL) was introduced while stirring, followed by tributylvinylstannane (1.79 g, 5.64 mmol) and a solution of 22 (700 mg, 2.82 mmol) in DMSO (5 mL). The resulting mixture was rigorously degassed six times by the freeze-pump-thaw process (−78° C. to 25° C., Ar). The reaction mixture was stirred at room temperature for 1 h, then stirred at 50° C. over night. After completion of the reaction, as indicated by TLC, the reaction mixture was cooled, diluted with Et$_2$O (10 mL), and washed with 5% aqueous NH$_4$OH (20 mL). The aqueous layer was extracted with Et$_2$O (3×20 mL), and the combined organic layers were washed with brine (2×10 mL), dried over Na$_2$SO$_4$. The solvent was removed in vacuo, and the residue was purified by flash column chromatography on silica gel (hexane/ethyl acetate=5/1) to give 17 (537 mg) in 82% yield as a colorless oil. 17: R$_f$=0.50 (hexane/ethyl acetate=2/1). $^1$H NMR (400 MHz, CDCl$_3$): δ 6.69-6.51 (m, 1H), 6.00 (d, J=10.8 Hz, 1H), 5.38 (s, 1H), 5.22 (d, J=16.0 Hz, 1H), 5.13 (d, J 9.8 Hz, 1H), 4.00 (s, 2H), 3.53 (s, 1H), 3.20 (s, 3H), 2.45-2.18 (m, 2H), 1.71 (s, 3H), 1.67 (s, 3H). $^{13}$C NMR (100 MHz, CDCl$_3$): δ 137.5, 136.5, 132.4, 128.4, 121.9, 117.1, 86.6, 68.8, 56.1, 32.2, 13.9, 11.2. IR (film): ν$_{max}$ 3389, 2923, 2855, 1640, 1599, 1446, 1380, 1306, 1089, 1011 cm$^{-1}$. [α]$^{25}_D$=+40.0 (c=0.7, MeOH). HR-MS (m/z): [M+Na]$^+$ calcd for C$_{12}$H$_{20}$O$_2$Na$^+$ 219.1356, found 219.1354. HPLC (Chiralpak-OD-H column, 99:1 hexane/ethanol, flow rate: 0.8 mL/min): t$_{major}$=19.659 min; t$_{minor}$=18.530 min, ee=98%.

Synthesis of ((2S,3S)-3-((R,E)-2-methoxy-3-methyl-hexa-3,5-dien-1-yl)-2-methyloxiran-2-yl)methanol (23)

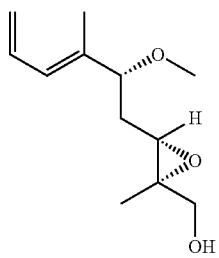

The alcohol 17 (465 mg, 2.37 mmol) was dissolved in CH$_2$Cl$_2$ (4 mL). To a suspension of flame-dried 4 Å molecular sieves (90 mg) in CH$_2$Cl$_2$ (8 mL) were sequentially added Ti(Oi-Pr)$_4$ (68 mg, 72 μL, 0.24 mmol), (+)-diethyl L-tartrate (59 mg, 49 μL, 0.28 mmol) and t-BuOOH (0.86 mL, 5.5 M in decane, 4.74 mmol) at −40° C. The mixture was stirred at that temperature for 10 min before the solution of 17 was added. The reaction mixture was stirred over night at same temperature before quenched with saturated aq. Na$_2$SO$_3$ (15 mL). After extraction with EtOAc (3×15 mL), the combined organic layers were washed with brine (5 mL) and dried over anhydrous Na$_2$SO$_4$ and filtered. The solvent was removed in vacuo, and the residue was purified by flash column chromatography on silica gel (hexane/ethyl acetate=4/1) to give 23 (478 mg) in 95% yield as a colorless oil. 23: R$_f$=0.52 (hexane/ethyl acetate=1/1). $^1$H NMR (400 MHz, CDCl$_3$): δ 6.72-6.47 (m, 1H), 6.07 (dd, J=10.9, 0.6 Hz, 1H), 5.23 (d, J=16.9 Hz, 1H), 5.15 (d, J=9.6 Hz, 1H), 3.75-3.61 (m, 2H), 3.61-3.47 (m, 1H), 3.22 (d, J=3.7 Hz, 3H), 3.08-3.00 (m, 1H), 1.94-1.85 (m, 1H), 1.85-1.76 (m, 1H), 1.72 (d, J 1.1 Hz, 3H), 1.27 (d, J=2.7 Hz, 3H). $^{13}$C NMR (100 MHz, CDCl$_3$): δ 136.7, 132.2, 128.9, 117.7, 84.7, 65.3, 60.6, 57.4, 56.0, 32.7, 14.3, 11.1. IR (film): ν$_{max}$ 3437, 2927, 2855, 1421, 1382, 1089, 1036, 988 cm$^{-1}$. [α]$^{25}_D$=+18.0 (c=0.2, MeOH). HR-MS (m/z): [M+Na]$^+$ calcd for C$_{12}$H$_{20}$O$_3$Na$^+$ 235.1305, found 235.1307. HPLC (Chiralpak-OD-H column, 99:1 hexane/isopropanol, flow rate: 0.8 mL/min): t$_{major}$=36.435 min; t$_{minor}$=34.677 min, ee>99%.

Synthesis of (2R,3S)-3-((R,E)-2-methoxy-3-methyl-hexa-3,5-dien-1-yl)-2-methyloxirane-2-carboxylic acid (14)

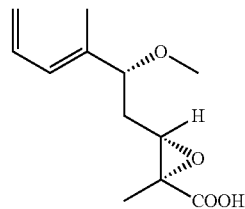

To a stirred solution of alcohol 23 (100 mg, 0.47 mmol) in CH$_2$Cl$_2$ (3 mL) was sequentially added phosphate buffer (pH=7.0, 3 mL), 2-azaadamantane N-oxyl (AZADO, 4 mg, 0.023 mmol), and PhI(OAc)$_2$ (454 mg, 1.41 mmol) at room temperature. The reaction mixture was stirred at the same temperature for 2 h before quenched with saturated aq. NaHSO$_3$ (5 mL) and extracted with DCM (3×10 mL). The combined organic phases were washed with brine (10 mL) and dried over anhydrous Na$_2$SO$_4$. The solvent was removed in vacuo, and the residue was purified by flash column chromatography on silica gel (hexane/ethyl acetate/acetic acid=100/25/1) to give 14 (59 mg) in 55% yield as a colorless oil. 14: R$_f$=0.52 (hexane/ethyl acetate/acetic acid=50/50/1). $^1$H NMR (400 MHz, CDCl$_3$): δ 8.83 (s, 1H), 6.69-6.47 (m, 1H), 6.08 (d, J=10.8 Hz, 1H), 5.25 (d, J=16.9 Hz, 1H), 5.17 (d, J=10.1 Hz, 1H), 3.72 (t, J=6.8 Hz, 1H), 3.24 (s, 1H), 3.21 (s, 3H), 1.97-1.75 (m, 2H), 1.71 (s, 3H), 1.53 (s, 3H). $^{13}$C NMR (100 MHz, CDCl$_3$): δ 175.3, 136.1, 132.0, 129.2, 118.2, 84.3, 60.2, 57.2, 56.1, 32.6, 13.1, 11.1. IR (film): ν$_{max}$ 2928, 1724, 1599, 1448, 1419, 1382, 1275, 1180, 1089, 988 cm$^{-1}$. [α]$^{25}_D$=+6.0 (c=0.1, MeOH). HR-MS (m/z): [M+Na]$^+$ calcd for C$_{12}$H$_{18}$O$_4$Na$^+$ 249.1097, found 249.1098.

Synthesis of (R)-benzyl 2-((2S,3S)-2-((((9H-fluoren-9-yl)methoxy)carbonyl)(methyl)amino)-3-methylpentanamido)-3-(4-hydroxyphenyl)propanoate (27)

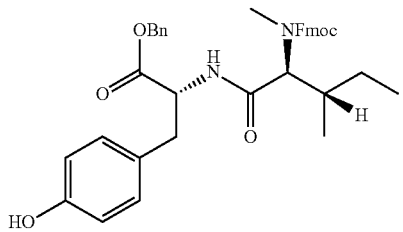

Compound 26 (271 mg, 1.0 mmol) and N-Fmoc-protected N-methyl-L-isoleucine (367 mg, 1.0 mmol) were dissolved in DCM (5 mL) at 0° C. After HBTU (560 mg, 1.5 mmol) and i-Pr$_2$NEt (0.3 mL, 2.0 mmol) were added, the reaction mixture was stirred at room temperature for 12 h before it was diluted with aqueous citric acid (5%, 5 mL). Layers were separated and the aqueous layer was further extracted with EtOAc (10 mL×2). The combined organic layers were washed with brine (3 mL), dried over Na$_2$SO$_4$. The solvent was removed in vacuo, and the residue was purified by flash column chromatography on silica gel (hexane/ethyl acetate=5/1) to give 27 (589 mg) in 95% yield as a colorless oil. 27: R$_f$=0.47 (hexane/ethyl acetate=2/1). $^1$H NMR (400 MHz, CDCl$_3$): δ 7.86-7.64 (m, 2H), 7.64-7.44 (m, 2H), 7.44-7.14 (m, 9H), 7.01-6.72 (m, 2H), 6.75-6.54 (m, 2H), 6.29 (s, 1H), 5.20-4.97 (m, 2H), 4.93-4.66 (m, 1H), 4.47-4.26 (m, 2H), 4.26-3.98 (m, 2H), 3.17-2.87 (m, 2H), 2.82 (s, 2.2H), 2.68 (s, 0.8H), 2.05 (s, 1H), 1.87-1.58 (m, 1H), 1.39-1.27 (m, 1H), 1.04-0.89 (m, 1H), 0.85 (t, J=7.2 Hz, 2H), 0.77 (d, J=6.4 Hz, 2H), 0.54 (t, J=6.7 Hz, 1H), 0.40 (d, J=5.9 Hz, 1H). $^{13}$C NMR (100 MHz, CDCl$_3$): δ 171.0, 170.1, 157.6, 155.2, 144.1, 143.8, 141.4, 141.3, 135.2, 130.2, 128.5, 128.4, 127.7, 127.1, 127.1, 125.1, 125.1, 120.0, 115.5, 68.0, 67.1, 63.8, 53.3, 47.2, 37.0, 31.6, 30.1, 24.5, 15.5, 10.4. IR (film): ν$_{max}$ 3301, 2964, 1740, 1666, 1614, 1515, 1450, 1309, 1265, 1223, 1170, 1106, 995 cm$^{-1}$. [α]$^{25}_D$=−49.5 (c=0.6, MeOH). HR-MS (m/z): [M+Na]$^+$ calcd for C$_{38}$H$_{40}$N$_2$O$_6$Na$^+$ 643.2779, found 643.2773.

(R)-2-((2S,3S)-2-((((9H-fluoren-9-yl)methoxy)carbonyl)(methyl)amino)-3-methylpentanamido)-3-(4-hydroxyphenyl)propanoic acid (28)

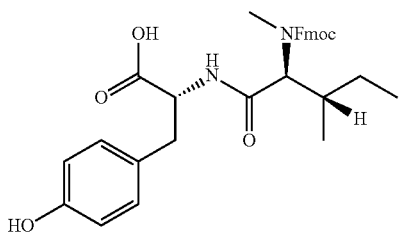

28

Compound 27 (620 mg, 1.0 mmol) was suspended together with Pd/C (106 mg, 10% on carbon) in EtOAc (30 mL), and the resulting mixture was stirred at room temperature under H$_2$ atmosphere for 4 h. After filtration through a pad of Celite and washing the Celite with MeOH (50 mL). The filtrate was removed in vacuo, and the residue was purified by flash column chromatography on silica gel (hexane/ethyl acetate/acetic acid=50/25/1) to give 28 (488 mg) in 92% yield as a white solid. 28: R$_f$=0.20 (hexane/ethyl acetate/acetic acid=25/25/1). $^1$H NMR (400 MHz, d$_4$-MeOH): δ 7.78 (d, J=7.5 Hz, 2H), 7.62-7.52 (m, 1.6H), 7.50 (d, J=7.4 Hz, 0.4H), 7.37 (t, J=7.5 Hz, 2H), 7.32-7.18 (m, 2H), 7.01 (d, J=7.8 Hz, 1.2H), 6.92 (d, J=7.5 Hz, 0.8H), 6.76-6.51 (m, 2H), 4.76-4.69 (m, 0.4H), 4.60-4.52 (m, 0.6H), 4.49-4.37 (m, 1.6H), 4.34 (s, 0.4H), 4.24 (t, J=5.6 Hz, 1H), 4.14 (d, J=10.9 Hz, 0.6H), 3.42-3.32 (m, 0.4H), 3.15-2.98 (m, 1H), 2.92-2.77 (m, 1H), 2.69 (d, J=14.9 Hz, 3H), 1.89 (s, 0.6H), 1.69 (s, 0.4H), 1.21 (s, 1H), 0.89 (s, 1H), 0.81 (t, J=6.7 Hz, 2H), 0.63 (d, J=6.0 Hz, 3H), 0.46 (d, J=5.7 Hz, 2H). $^{13}$C NMR (100 MHz, d$_4$-MeOH): δ 173.1, 170.6, 155.9, 144.0, 141.3, 129.8, 127.4, 127.4, 127.0, 126.8, 124.6, 119.5, 114.8, 67.4, 66.6, 63.0, 53.7, 36.0, 32.0, 29.0, 24.2, 14.3, 9.4. IR (film): ν$_{max}$ 3320, 2963, 1660, 1614, 1515, 1449, 1402, 1310, 1224, 1171 cm$^{-1}$. [α]$^{25}_D$=−50.5 (c=0.9, MeOH). HR-MS (m/z): [M+Na]$^+$ calcd for C$_{31}$H$_{34}$N$_2$O$_6$Na$^+$ 553.2309, found 553.2301.

Synthesis of (S)-(1S,2R)-2-methyl-1-phenylbut-3-en-1-yl 2-((tert-butoxycarbonyl) amino)-3-hydroxy-3-methylbutanoate (15)

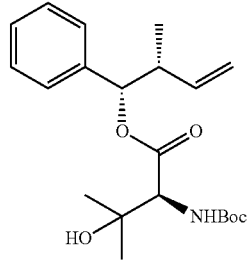

15

A solution of 16 (300 mg, 1.85 mmol, prepared according to ref. 10 with [α]$^{25}_D$=+65.0 (c=0.9, MeOH)), Ph$_3$P (1.60 g, 6.11 mmol), and amino acid 24 (475 mg, 2.04 mmol) in 10 mL mixture of CH$_2$Cl$_2$/THF (1:1) was cooled to −20° C., and treated with diisopropylazodicarboxylate (DIAD, 1.12 g, 1.10 mL, 5.55 mmol) dropwise over 30 min. After being stirred at −20° C. for 30 min, the reaction mixture was stirred at room temperature overnight. The reaction mixture was quenched by addition of a saturated aqueous NH$_4$Cl (10 mL), and extracted with DCM (4×10 mL). The combined organic layers were washed with brine (5 mL), and dried over Na$_2$SO$_4$. The solvent was removed in vacuo, and the residue was purified by flash column chromatography on silica gel (hexane/ethyl acetate=8/1) to give 15 (342 mg) in 72% yield as a colorless oil. 15: R$_f$=0.38 (hexane/ethyl acetate=4/1). $^1$H NMR (500 MHz, CDCl$_3$): δ 7.34-7.24 (m, 5H), 5.69 (d, J=7.0 Hz, 1H), 5.67-5.60 (m, 1H), 5.37 (d, J=7.5 Hz, 1H), 4.98 (d, J=15.0 Hz, 2H), 4.23 (d, J=9.0 Hz, 1H), 2.76 (dd, J=14.0, 7.0 Hz, 1H), 2.59 (s, 1H), 1.45 (s, 9H), 1.28 (d, J=6.0 Hz, 1H), 1.19 (s, 3H), 1.09 (s, 3H), 1.08 (s, 3H). $^{13}$C NMR (125 MHz, CDCl$_3$): δ 171.5, 155.7, 138.8, 138.0, 128.2 (2C), 128.1, 127.3 (2C), 116.1, 80.4, 71.8, 61.1, 42.7, 28.3 (3C), 26.9, 26.1, 21.6, 15.3. IR (film): ν$_{max}$ 3441, 2978, 1714, 1495, 1367, 1246, 1157, 1050, 914 cm$^{-1}$. [α]$^{25}_D$=−43.0 (c=1.0, MeOH). HR-MS (m/z): [M+Na]$^+$ calcd for C$_{21}$H$_{31}$NO$_5$Na$^+$ 400.2094, found 400.2095.

Synthesis of (5S,8R,11S)-(1S,2R)-2-methyl-1-phenylbut-3-en-1-yl 5-((S)-sec-butyl)-1-(9H-fluoren-9-yl)-8-(4-hydroxybenzyl)-11-(2-hydroxypropan-2-yl)-4-methyl-3,6,9-trioxo-2-oxa-4,7,10-triazadodecan-12-oate (29)

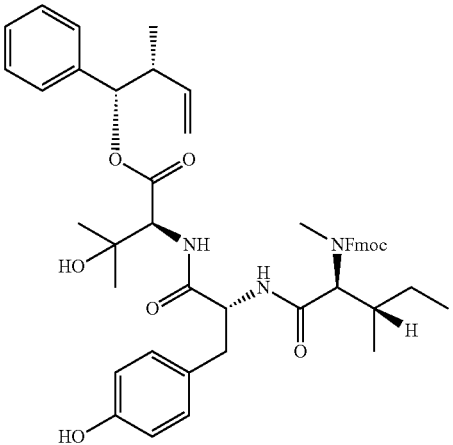

29

To a solution of 15 (35 mg, 0.093 mmol) in 1,4-dioxane (2 mL) was added HCl (4 M in 1,4-dioxane, 2 mL) at 0° C. The reaction mixture was stirred at room temperature for 3 h before concentrated in vacuo to produce the amine intermediate as its HCl salt. Benzene (2 mL) was added to the residue, and this solution was concentrated in vacuo. This procedure was repeated twice to ensure complete removal of excess HCl. The residue was dried under high vacuum for 1 h before used in the next step.

The above residue and 28 (49 mg, 0.093 mmol) were dissolved in THF (1 mL) at 0° C. After HBTU (53 mg, 0.14 mmol) and DIPEA (0.05 mL, 0.28 mmol) were added sequentially, the reaction mixture was warmed to room temperature and stirred for 3 h before it was diluted with aqueous citric acid (5%, 4 mL) and EtOAc (10 mL). Layers were separated and the aqueous layer was extracted with EtOAc (10 mL×2). The combined organic layers were washed with aqueous brine (3 mL), dried over $Na_2SO_4$. The solvent was removed in vacuo, and the residue was purified through preparative TLC (hexane/ethyl acetate=1/1) to afford 29 (44 mg) in 60% yield as a white powder. 29: $R_f$=0.20 (hexane/ethyl acetate=1/1). $^1$H NMR (600 MHz, $d_4$-MeOH): δ 7.94-7.72 (m, 2H), 7.72-7.52 (m, 2H), 7.47-7.37 (m, 2H), 7.37-7.13 (m, 6H), 7.13-6.94 (m, 2H), 6.71 (d, J=7.9 Hz, 2H), 5.74-5.37 (m, 2H), 4.90 (d, J=15.7 Hz, 1H), 4.72 (s, 0.3H), 4.71-4.66 (m, 0.7H), 4.63 (s, 0.3H), 4.56-4.49 (m, 1H), 4.41 (s, 0.3H), 4.37 (s, 0.7H), 4.36-4.31 (m, 1H), 4.24 (s, 0.7H), 4.18 (d, J=10.9 Hz, 0.7H), 3.16-3.04 (m, 1H), 2.90-2.59 (m, 5H), 1.87 (s, 0.7H), 1.73 (s, 0.3H), 1.31 (s, 1H), 1.28-1.15 (m, 2H), 1.14-0.97 (m, 9H), 0.91 (d, J=7.0 Hz, 1H), 0.84 (t, J=6.9 Hz, 2.2H), 0.70 (s, 0.8H), 0.55 (d, J=6.3 Hz, 2.2H), 0.45 (s, 0.8H). $^{13}$C NMR (125 MHz, $CDCl_3$): δ 171.1, 170.8, 170.5, 157.6, 155.3, 143.9, 143.8, 141.4, 141.3, 138.5, 137.9, 130.1, 128.1, 127.7, 127.5, 127.1, 125.1, 125.0, 120.0, 116.1, 115.7, 80.8, 71.7, 68.0, 64.0, 60.1, 54.8, 47.2, 42.6, 36.9, 32.2, 30.3, 26.6, 26.6, 24.8, 15.6, 15.3, 10.5. IR (film): $ν_{max}$ 3331, 2965, 2927, 1666, 1516, 1451, 1311, 1196, 1155, 994, 740 cm$^{-1}$. $[α]^{25}_D$=−45.7 (c=1.0, MeOH). HR-MS (m/z): [M+Na]$^+$ calcd for $C_{47}H_{55}N_3O_8Na^+$812.3881, found 812.3888.

Synthesis of (S)-(1S,2R)-2-methyl-1-phenylbut-3-en-1-yl 3-hydroxy-2-((R)-3-(4-hydroxyphenyl)-2-((2S,3S)-3-methyl-2-(methylamino)pentanamido)propanamido)-3-methylbutanoate (13)

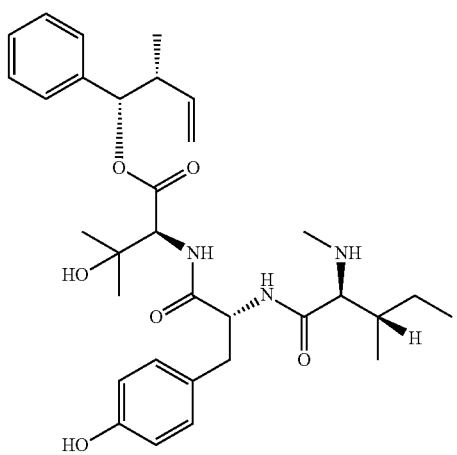

13

To a solution of 29 (44 mg, 0.056 mmol) in MeCN (2 mL) was added $Et_2NH$ (1 mL) at room temperature. The solution was stirred for 1 h and then concentrated to dryness. The residue was purified through preparative TLC (DCM/MeOH=10/1) to afford 13 (26 mg) in 82% yield as a white powder. 13: $R_f$=0.38 (DCM/MeOH=10/1). $^1$H NMR (400 MHz, $d_4$-MeOH): δ 7.37-7.23 (m, 5H), 7.14-7.05 (m, 2H), 6.83-6.52 (m, 2H), 5.69-5.57 (m, 2H), 5.00-4.88 (m, 2H), 4.78 (dd, J=10.1 Hz, 5.4 Hz, 1H), 4.41 (s, 1H), 3.11 (dd, J=14.1 Hz, 5.4 Hz, 1H), 2.93 (d, J=5.4 Hz, 1H), 2.85-2.70 (m, 2H), 2.25 (s, 3H), 1.60-1.47 (m, 1H), 1.36-1.27 (m, 1H), 1.18-1.04 (m, 9H), 0.92-0.83 (m, 1H), 0.79 (dd, J=7.3 Hz, 6.4 Hz, 3H), 0.73 (d, J=6.9 Hz, 3H). $^{13}$C NMR (100 MHz, $d_4$-MeOH): δ 173.2, 172.3, 169.7, 156.1, 138.9 (2C), 138.4, 129.9 (2C), 127.7 (2C), 127.6, 127.5, 127.3 (2C), 114.9, 114.9, 80.4, 70.7, 68.4, 60.8, 54.5, 42.9, 37.6, 36.6, 33.7, 26.1, 25.8, 24.9, 14.9, 14.0, 10.5. IR (film): $ν_{max}$ 3284, 2963, 2925, 1736, 1639, 1515, 1453, 1378, 1201 cm$^{-1}$. $[α]^{25}_D$=+27 (c=0.1, MeOH). HR-MS (m/z): [M+Na]$^+$ calcd for $C_{32}H_{45}N_3O_6Na^+$590.3201, found 590.3200.

Synthesis of (S)-(1S,2R)-2-methyl-1-phenylbut-3-en-1-yl 3-hydroxy-2-((R)-3-(4-hydroxyphenyl)-2-((2S,3S)-2-((2R,3S)-3-((R,E)-2-methoxy-3-methylhexa-3,5-dien-1-yl)-N,2-dimethyloxirane-2-carboxamido)-3-methylpentanamido)propanamido)-3-methylbutanoate (12)

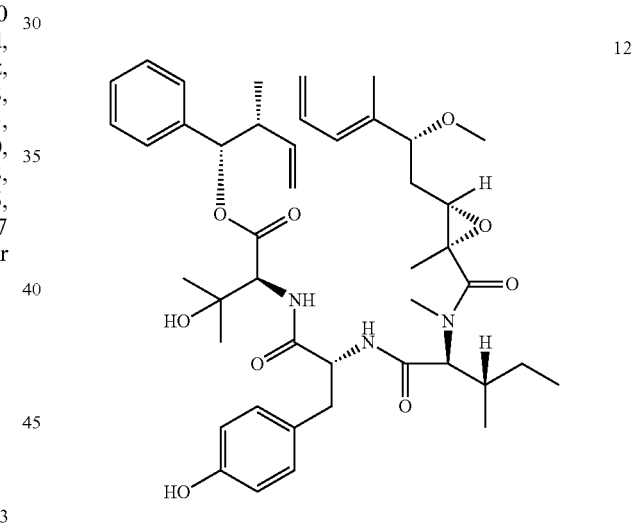

12

To a solution of 14 (16 mg, 0.066 mmol) in dry DCM (2 mL) was added 1-chloro-N,N,2-trimethyl-1-propenylamine (26 mg, 26 µL, 0.20 mmol) at 0° C. The reaction mixture was stirred at room temperature for 5 h before concentrated in vacuo to produce the acyl chloride 31. The acyl chloride 31 was dried under high vacuum for 15 min and used directly for the next step.

To a solution of 13 (31 mg, 0.055 mmol) in dry THF (2 mL) was added DIPEA (43 mg, 55 µL, 0.33 mmol) and the above acyl chloride 31 (dissolved in 1 mL dry DCM) sequentially at −20° C. The reaction mixture was stirred at the same temperature for 10 min before quenched by addition of a saturated aqueous $NH_4Cl$ (0.1 mL). The solvent was removed in vacuo, and the residue was purified by flash column chromatography on silica gel (hexane/ethyl acetate=1/1) to give 12 (34 mg) in 80% yield as a colorless oil. 12: $R_f$=0.42 (hexane/ethyl acetate=1/2). $^1$H NMR (400 MHz, $CDCl_3$): δ 7.34-7.27 (m, 5H), 7.05 (d, J=8.4 Hz, 2H), 6.87 (d, J=8.4 Hz, 1H), 6.75 (d, J=8.0 Hz, 2H), 6.64-6.49 (m, 2H), 6.06 (d, J=10.9 Hz, 1H), 5.63 (d, J=7.8 Hz, 1H), 5.61-5.51 (m, 1H), 5.22 (d, J=16.9 Hz, 1H), 5.14 (d, J=10.2 Hz, 1H), 4.98 (d, J=4.5 Hz, 1H), 4.95 (s, 1H), 4.71-4.59 (m, 1H), 4.44 (d, J=8.4 Hz, 1H), 4.34 (d, J=11.0 Hz, 1H), 3.87-3.69 (m, 1H), 3.18 (s, 3H), 3.16-3.06 (m, 2H), 3.01 (s, 3H), 2.82-2.70 (m, 1H), 2.16-2.01 (m, 1H), 1.88-1.82 (m, 1H), 1.79-1.73 (m, 1H), 1.71 (s, 3H), 1.44 (s, 3H), 1.12 (d, J=6.7 Hz, 3H), 1.07 (s, 3H), 1.01 (s, 3H), 0.96-0.88 (m, 1H), 0.83 (t, J=7.2 Hz, 3H), 0.71 (d, J=6.4 Hz, 3H). $^{13}$C NMR (100 MHz, CDCl$_3$): δ 171.8, 170.8, 170.5, 170.1, 155.0, 138.6 (2C), 138.0, 136.5, 132.2, 130.2 (2C), 128.8, 128.1 (2C), 127.6 (2C), 118.0, 116.2 (2C), 115.8 (2C), 84.5, 80.8, 71.6, 62.0, 60.4, 60.1, 59.6, 56.1, 54.7, 42.7, 36.5, 33.0, 31.6, 31.0, 29.7, 26.8, 24.7, 15.8, 15.5, 14.9, 11.4, 10.5. IR (film): $v_{max}$ 3314, 2980, 2928, 1740, 1637, 1516, 1452, 1379, 1202, 1151, 1088 cm$^{-1}$. $[\alpha]^{25}_D$=−42 (c=0.3, MeOH). HR-MS (m/z): [M+Na]$^+$ calcd for C$_{44}$H$_{61}$N$_3$O$_9$Na$^+$ 798.4300, found 798.4302.

Synthesis of (1R,4S,7R,10S,13S,14R,15E,17E,19R,21S)-4-((S)-sec-butyl)-7-(4-hydroxybenzyl)-10-(2-hydroxypropan-2-yl)-19-methoxy-1,3,14,18-tetramethyl-13-phenyl-12,22-dioxa-3,6,9-triazabicyclo[19.1.0]docosa-15,17-diene-2,5,8,11-tetraone (nannocystin A0 (3))

(3)

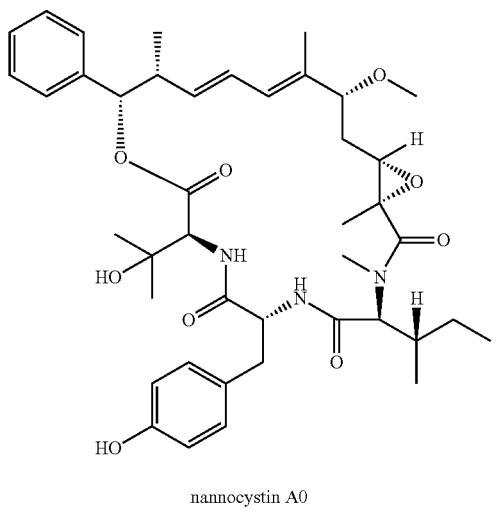

nannocystin A0

To a solution of 12 (14 mg, 0.018 mmol) in toluene (140 mL) was added Hoveyda-Grubbs 2$^{nd}$ generation catalyst (2.3 mg, 0.0036 mmol), and the reaction mixture was stirred at 60° C. for 2.5 h under argon atmosphere. After cooling to 0° C., ethyl vinyl ether (5 mL) was added to the reaction, and stirred for 10 min. The mixture was concentrated in vacuo. The residue was purified through reverse-phase preparative TLC (RP-18 F$_{254S}$) (MeCN/H$_2$O=3/2) to afford 3 (11 mg) in 79% yield as a white solid as a 4.6:1 mixture. The mixture was separated by semi-preparative HPLC (Gemini 5 u C18 110A column (10.0×150 mm, 5 micron), 60:40 water/acetonitrile, flow rate: 4.0 mL/min). $^1$H NMR (600 MHz, d$_6$-DMSO): δ 9.04 (s, 1H), 8.60 (d, J=9.9 Hz, 1H), 7.91 (d, J=9.5 Hz, 1H), 7.55 (d, J=7.6 Hz, 2H), 7.32 (t, J=7.6 Hz, 2H), 7.25 (t, J=7.3 Hz, 1H), 7.09 (d, J=8.5 Hz, 2H), 6.55 (d, J=8.5 Hz, 2H), 6.44-6.31 (m, 1H), 6.21-6.13 (m, 1H), 6.11 (d, J=10.7 Hz, 1H), 5.89 (s, 1H), 5.09 (s, 1H), 4.77-4.69 (m, 1H), 4.67 (d, J=10.0 Hz, 1H), 4.46 (d, J=11.3 Hz, 1H), 3.61 (dd, J=10.4, 3.2 Hz, 1H), 3.09 (s, 3H), 2.97 (s, 3H), 2.88-2.75 (m, 1H), 2.68-2.59 (m, 2H), 2.53-2.45 (m, 1H) 2.13-2.04 (m, 1H), 1.69 (s, 3H), 1.50-1.43 (m, 1H), 1.42 (s, 3H), 1.21-1.15 (m, 1H), 1.13 (s, 3H), 1.01 (s, 3H), 0.96 (d, J=6.8 Hz, 3H), 0.88-0.81 (m, 1H), 0.75 (t, J=7.4 Hz, 3H), 0.29 (d, J=6.6 Hz, 3H). $^{13}$C NMR (150 MHz, DMSO): δ 171.5, 171.1, 169.7, 169.1, 156.1, 140.4, 138.9, 133.8, 130.9 (2C), 129.4, 128.2, 128.1 (2C), 127.4, 126.4 (2C), 125.1, 114.9 (2C), 84.4, 79.3, 72.4, 61.8, 59.7, 59.5, 58.5, 55.6, 53.2, 42.4, 38.1, 31.6, 31.0, 30.2, 28.7, 24.8, 24.7, 15.3, 15.1, 11.1, 10.5, 10.0. IR (film): $v_{max}$ 3345, 2923, 2853, 1740, 1656, 1615, 1512, 1459, 1379, 1262, 1095 cm$^{-1}$. $[\alpha]^{25}_D$=−22 (c=0.21, DMSO). HR-MS (m/z): [M+Na]$^+$ calcd for C$_{42}$H$_{57}$N$_3$O$_9$Na$^+$ 770.3987, found 770.3983.

(R)-benzyl 2-amino-3-(3,5-dichloro-4-hydroxyphenyl)propanoate (33)

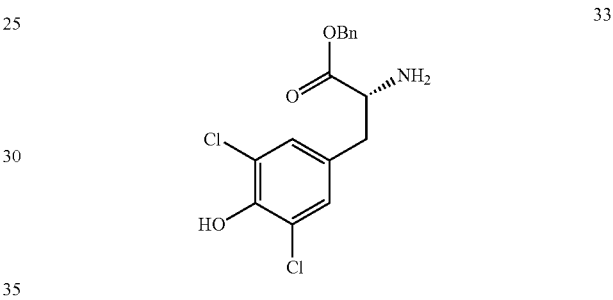

33

To a solution of (R)-benzyl 2-amino-3-(4-hydroxyphenyl)propanoate (3.00 g, 11.05 mmol) in 1.0 M HCl in AcOH (50 ml) was dropped SO$_2$Cl$_2$ (5.40 ml, 66.30 mmol) during 30 min. After the mixture was stirred for 1 h at 70° C. and for 2 h at room temperature, it was diluted with ether (150 ml) and allowed to stand for 15 min. The reaction was allowed to cool to room temperature and concentrated, and the residue was purified by flash column chromatography on silica gel (DCM/MeOH=30/1) to give 33 (3.00 g) in 80% yield as a pale yellow solid. 33: R$_f$=0.82 (silica gel, DCM/MeOH=10/1). $^1$H NMR (400 MHz, CDCl$_3$): δ 7.48-7.21 (m, 5H), 7.04 (s, 2H), 5.16 (q, J=12.1 Hz, 2H), 3.81-3.69 (m, 1H), 3.38 (s, 2H), 3.05-2.93 (m, 1H), 2.76-2.65 (m, 1H). $^{13}$C NMR (100 MHz, CDCl$_3$): δ 174.4, 147.1, 135.2, 129.8, 128.9 (2C), 128.7 (2C), 128.6 (2C), 128.4 (2C), 121.4, 67.1, 55.4, 39.2. IR (film): $v_{max}$ 3296, 2932, 1749, 1443, 1315, 1284, 1199, 1136 cm$^{-1}$. $[\alpha]^{25}_D$=+3.3 (c=0.66, CHCl$_3$). HR-MS (m/z): [M+Na]$^+$ calcd for C$_{16}$H$_{15}$Cl$_2$NO$_3$Na$^+$ 362.0321, found 362.0321.

31

(R)-benzyl 2-((2S,3S)-2-((((9H-fluoren-9-yl)methoxy)carbonyl)(methyl)amino)-3-methylpentanamido)-3-(3,5-dichloro-4-hydroxyphenyl)propanoate (S1)

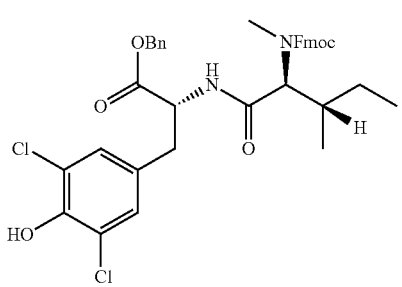

Compound 33 (500 mg, 1.47 mmol) and N-Fmoc-protected N-methyl-L-isoleucine (541 mg, 1.47 mmol) were dissolved in THF (5 mL) at 0° C. After HBTU (839 mg, 2.21 mmol) and i-Pr$_2$NEt (0.73 mL, 4.42 mmol) were added, the reaction mixture was stirred at room temperature for 4 h before it was diluted with aqueous citric acid (5%, 5 mL). Layers were separated and the aqueous layer was further extracted with EtOAc (10 mL×2). The combined organic layers were washed with brine (3 mL), dried over Na$_2$SO$_4$. The solvent was removed in vacuo, and the residue was purified by flash column chromatography on silica gel (hexane/ethyl acetate=5/1) to give S1 (913 mg) in 90% yield as a colorless oil. S1: R$_f$=0.50 (hexane/ethyl acetate=2/1). $^1$H NMR (600 MHz, CDCl$_3$): δ 7.88 (d, J=7.3 Hz, 0.2H), 7.81 (d, J=7.7 Hz, 0.3H), 7.80-7.75 (m, 1H), 7.73 (d, J=7.2 Hz, 0.3H), 7.58 (d, J=7.4 Hz, 0.9H), 7.53 (d, J=7.4 Hz, 0.2H), 7.49 (d, J=7.2 Hz, 0.2H), 7.41 (t, J=7.5 Hz, 1.3H), 7.34-7.29 (m, 2.3H), 7.27-7.24 (m, 1.1H), 7.22 (d, J=6.6 Hz, 0.8H), 7.14 (s, 0.9H), 7.02 (s, 0.5H), 6.94 (d, J=8.3 Hz, 0.4H), 6.80 (d, J=7.9 Hz, 0.3H), 6.72 (d, J=8.1 Hz, 0.4H), 5.97-5.91 (m, 0.6H), 5.69 (d, J=7.8 Hz, 0.3H), 5.65-5.59 (m, 0.3H), 5.59-5.54 (m, 0.5H), 5.54-5.48 (m, 0.5H), 5.01 (d, J=6.6 Hz, 0.2H), 4.98 (s, 0.5H), 4.93 (s, 0.5H), 4.91-4.88 (m, 0.6H), 4.85 (d, J=8.4 Hz, 0.3H), 4.73-4.69 (m, 0.4H), 4.68-4.64 (m, 0.3H), 4.51-4.47 (m, 0.5H), 4.42 (d, J=8.4 Hz, 0.5H), 4.40 (d, J=8.3 Hz, 0.3H), 4.34-4.29 (m, 0.6H), 4.25-4.21 (m, 0.8H), 4.06 (d, J=11.2 Hz, 0.5H), 3.17-3.08 (m, 0.7H), 2.96 (d, J=11.2 Hz, 0.3H), 2.91-2.88 (m, 1.0H), 2.88-2.83 (m, 1.0H), 2.76-2.72 (m, 0.5H), 2.65 (s, 0.9H), 2.53 (s, 0.4H), 2.45 (s, 0.3H), 2.07-2.01 (m, 0.5H), 1.88 (s, 0.8H), 1.67 (d, J=7.1 Hz, 0.4H), 1.37-1.30 (m, 0.8H), 1.30-1.25 (m, 1.2H), 1.16 (d, J=6.5 Hz, 0.9H), 1.08 (s, 0.6H), 1.06-1.02 (m, 3H), 0.99 (s, 1.4H), 0.88 (t, J=7.3 Hz, 1.5H), 0.74 (d, J=6.5 Hz, 1.3H), 0.51 (t, J=7.2 Hz, 0.7H), 0.34 (d, J=6.3 Hz, 0.7H). $^{13}$C NMR (100 MHz, CDCl$_3$): δ 170.7, 170.5, 170.4, 157.6, 146.8, 143.9, 143.8, 141.3, 138.4, 137.8, 130.2, 128.9, 128.2, 128.1, 127.7, 127.6, 127.5, 125.0, 125.0, 121.1, 120.0, 116.2, 80.9, 77.2, 71.6, 68.0, 64.2, 60.1, 54.0, 47.2, 42.6, 36.2, 32.1, 30.4, 26.7, 26.6, 24.8, 15.7, 15.4, 10.5. IR (film): $\nu_{max}$ 3331, 2964, 1740, 1673, 1488, 1451, 1309, 1242, 1154, 736 cm$^{-1}$; $[\alpha]^{25}_D$=-50.3 (c=0.6, CHCl$_3$); HR-MS (m/z): [M+Na]$^+$ calcd for C$_{38}$H$_{38}$Cl$_2$N$_2$O$_6$Na$^+$ 711.1999, found 711.2001.

32

(R)-2-((2S,3S)-2-((((9H-fluoren-9-yl)methoxy)carbonyl)(methyl)amino)-3-methylpentanamido)-3-(3,5-dichloro-4-hydroxyphenyl)propanoic acid (S2)

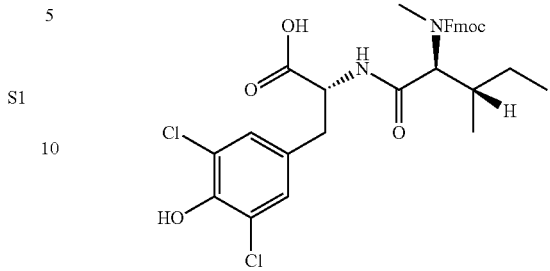

Compound S1 (700 mg, 0.99 mmol) was suspended together with Pd/C (105 mg, 10% on carbon) in EtOAc (20 mL), and the resulting mixture was stirred at room temperature under H$_2$ atmosphere for 2 h. After filtration through a pad of Celite and washing the Celite with MeOH (50 mL). The filtrate was removed in vacuo, and the residue was purified by flash column chromatography on silica gel (hexane/ethyl acetate/acetic acid=50/25/1) to give S2 (488 mg) in 89% yield as a colorless oil. S2: R$_f$=0.25 (hexane/ethyl acetate/acetic acid=25/25/1). $^1$H NMR (600 MHz, CDCl$_3$): δ 7.79-7.75 (m, 0.5H), 7.75-7.71 (m, 1.4H), 7.53-7.49 (m, 1.7H), 7.39-7.34 (m, 1.8H), 7.28-7.25 (m, 1.2H), 7.20-7.18 (m, 0.3H), 7.13-7.09 (m, 0.6H), 7.08 (s, 1H), 6.95 (s, 0.4H), 5.19 (d, J=8.1 Hz, 0.3H), 4.87-4.81 (m, 0.4H), 4.71-4.63 (m, 0.7H), 4.55-4.49 (m, 0.4H), 4.43-4.38 (m, 0.8H), 4.32-4.25 (m, 1H), 4.21-4.14 (m, 1.7H), 3.09 (d, J=11.2 Hz, 0.4H), 3.06-2.97 (m, 1H), 2.90-2.84 (m, 2.7H), 2.62 (d, J=6.0 Hz, 0.8H), 2.42 (s, 0.1H), 2.36 (s, 0.3H), 2.06 (d, J=7.4 Hz, 0.7H), 2.03 (s, 0.5H), 1.72-1.67 (m, 0.3H), 1.35-1.29 (m, 1.1H), 1.00-0.92 (m, 1.2H), 0.87 (t, J=7.4 Hz, 2.2H), 0.81 (d, J=6.5 Hz, 2H), 0.55 (t, J=7.4 Hz, 0.7H), 0.43 (d, J=6.4 Hz, 0.7H). $^{13}$C NMR (100 MHz, CDCl$_3$): δ 176.4, 174.1, 170.2, 157.6, 146.9, 143.7, 143.5, 141.3, 141.3, 129.9, 129.1, 127.8, 127.1, 124.9, 124.9, 121.1, 120.0, 120.0, 68.1, 63.6, 53.4, 47.1, 36.3, 32.0, 30.1, 24.6, 20.8, 15.3, 10.4. IR (film): $\nu_{max}$ 2965, 1672, 1488, 1450, 1406, 1265, 1155 cm$^{-1}$; $[\alpha]^{25}_D$=-63.2 (c=0.56, CHCl$_3$); HR-MS (m/z): [M+Na]$^+$ calcd for C$_{31}$H$_{32}$Cl$_2$N$_2$O$_6$Na$^+$ 621.1530, found 621.1532.

(5S,8R,11S)-(1S,2R)-2-methyl-1-phenylbut-3-en-1-yl 5-((S)-sec-butyl)-8-(3,5-dichloro-4-hydroxybenzyl)-1-(9H-fluoren-9-yl)-11-(2-hydroxypropan-2-yl)-4-methyl-3,6,9-trioxo-2-oxa-4,7,10-triazadodecan-12-oate (S3)

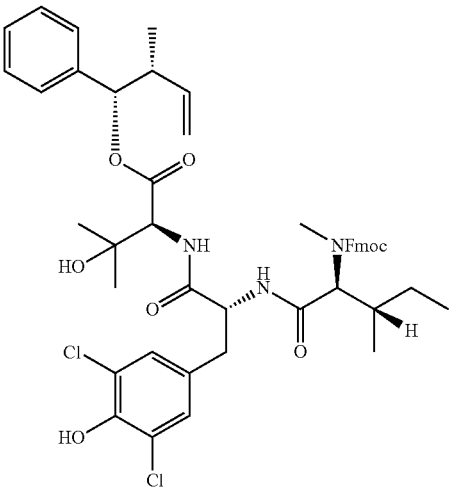

To a solution of 15 (64 mg, 0.17 mmol) in 1,4-dioxane (2 mL) was added HCl (4 M in 1,4-dioxane, 2 mL) at 0° C. The reaction mixture was stirred at room temperature for 3 h before concentrated in vacuo to produce the amine intermediate as its HCl salt. Benzene (2 mL) was added to the residue, and this solution was concentrated in vacuo. This procedure was repeated twice to ensure complete removal of excess HCl. The residue was dried under high vacuum for 1 h before used in the next step.

The above residue and S2 (98 mg, 0.16 mmol) were dissolved in THF (2 mL) at 0° C. After HBTU (91 mg, 0.24 mmol) and DIPEA (0.08 mL, 0.48 mmol) were added sequentially, the reaction mixture was warmed to room temperature and stirred for 4 h before it was diluted with aqueous citric acid (5%, 4 mL) and EtOAc (10 mL). Layers were separated and the aqueous layer was extracted with EtOAc (10 mL×2). The combined organic layers were washed with aqueous brine (3 mL), dried over $Na_2SO_4$. The solvent was removed in vacuo, and the residue was purified through preparative TLC (hexane/ethyl acetate=1/1) to afford S3 (70 mg) in 51% yield as a colorless oil. S3: $R_f$=0.65 (hexane/ethyl acetate=1/1). $^1$H NMR (500 MHz, $CDCl_3$): δ 7.77 (d, J=7.5 Hz, 2H), 7.64-7.53 (m, 1.4H), 7.51 (d, J=7.2 Hz, 0.4H), 7.46 (d, J=7.3 Hz, 0.4H), 7.44-7.36 (m, 2.6H), 7.36-7.27 (m, 4.4H), 7.25-7.14 (m, 1.6H), 6.96 (s, 1.3H), 6.91 (s, 0.7H), 6.71 (d, J=7.7 Hz, 0.7H), 5.86 (s, 0.3H), 5.81 (s, 0.6H), 5.20 (d, J=11.7 Hz, 0.7H), 5.14-5.05 (m, 1H), 5.02 (d, J=12.1 Hz, 0.7H), 4.93-4.81 (m, 0.3H), 4.81-4.72 (m, 0.6H), 4.64-4.45 (m, 0.7H), 4.45-4.32 (m, 1.3H), 4.25 (t, J=7.0 Hz, 0.7H), 4.22-4.08 (m, 1H), 3.10 (d, J=11.0 Hz, 0.4H), 3.06-2.96 (m, 1H), 2.96-2.86 (m, 0.7H), 2.84 (s, 2H), 2.74-2.67 (m, 0.4H), 2.66 (s, 1H), 2.16-2.06 (m, 0.6H), 1.71 (s, 0.4H), 1.65 (s, 1H), 1.41-1.31 (m, 0.7H), 1.05-0.93 (m, 1H), 0.89 (t, J=7.3 Hz, 2H), 0.85 (d, J=6.4 Hz, 2H), 0.58 (t, J=7.1 Hz, 1H), 0.44 (d, J=6.1 Hz, 1H). $^{13}$C NMR (125 MHz, $CDCl_3$): δ 170.4, 170.1, 157.5, 146.8, 144.0, 143.8, 141.4, 141.3, 134.9, 128.9, 128.6, 128.6, 128.4, 127.7, 127.0, 125.0, 121.0, 120.0, 67.9, 67.4, 63.8, 53.0, 47.2, 36.6, 31.6, 30.2, 24.5, 15.6, 10.5. IR (film): $v_{max}$ 3316, 2967, 2932, 1740, 1659, 1521, 1489, 1451, 1311, 1154 $cm^{-1}$; $[α]^{25}_D$=-48.6 (c=0.50, $CHCl_3$); HR-MS (m/z): $[M+Na]^+$ calcd for $C_{47}H_{53}Cl_2N_3O_8Na^+$ 880.3102, found 880.3101.

(S)-(1S,2R)-2-methyl-1-phenylbut-3-en-1-yl-2-((R)-3-(3,5-dichloro-4-hydroxyphenyl)-2-((2S,3S)-3-methyl-2-(methylamino)pentanamido)propanamido)-3-hydroxy-3-methylbutanoate (S4)

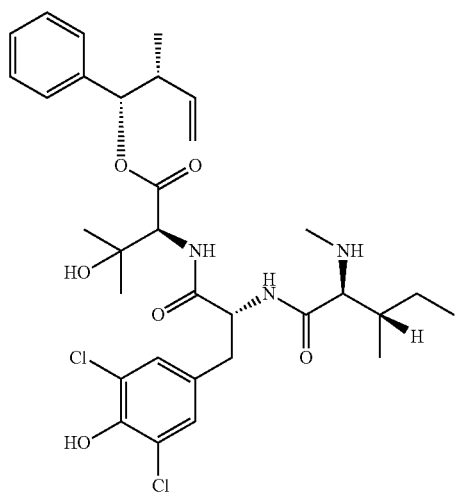

S4

To a solution of S3 (20 mg, 0.023 mmol) in MeCN (2 mL) was added $Et_2NH$ (1 mL) at room temperature. The solution was stirred for 1 h then concentrated to dryness. The residue was purified through preparative TLC (DCM/MeOH=20/1) to afford S4 (11 mg) in 74% yield as a colorless oil. S4: $R_f$=0.60 (DCM/MeOH=6/1). $^1$H NMR (600 MHz, $CDCl_3$): δ 7.72 (d, J=8.0 Hz, 1H), 7.39-7.26 (m, 5H), 7.26-7.19 (m, 1H), 7.16 (s, 2H), 5.62 (d, J=8.0 Hz, 1H), 5.60-5.52 (m, 1H), 5.00-4.96 (m, 1H), 4.95 (s, 1H), 4.78-4.69 (m, 1H), 4.46 (d, J=8.4 Hz, 1H), 3.49 (d, J=7.0 Hz, 1H), 3.13 (d, J=6.1 Hz, 1H), 3.10 (d, J=6.1 Hz, 1H), 2.97 (d, J=8.1 Hz, 1H), 2.95 (d, J=8.1 Hz, 1H), 2.85 (d, J=4.4 Hz, 1H), 2.81-2.73 (m, 1H), 2.23 (s, 3H), 1.82-1.74 (m, 1H), 1.45-1.35 (m, 1H), 1.11 (d, J=6.7 Hz, 3H), 1.08 (s, 3H), 1.02 (s, 3H), 0.91 (d, J=6.9 Hz, 3H), 0.85 (t, J=7.4 Hz, 3H). $^{13}$C NMR (150 MHz, $CDCl_3$): δ 172.6, 169.7, 169.3, 145.8, 137.2 (2C), 136.6, 128.7, 127.8 (2C), 126.9, 126.9 (2C), 126.3 (2C), 120.1, 114.9, 79.6, 70.4, 68.3, 58.9, 52.5, 41.3, 36.8, 35.3, 34.6, 25.5, 25.3, 23.9, 14.5, 14.4, 10.5. IR (film): $v_{max}$ 3300, 2969, 2932, 1737, 1648, 1532, 1490, 1462, 1283, 1193, 1155 $cm^{-1}$; $[α]^{25}_D$=+30 (c=0.20, $CHCl_3$); HR-MS (m/z): $[M+H]^+$ calcd for $C_{32}H_{44}Cl_2N_3O_6^+$ 636.2602, found 636.2601.

(S)-(1S,2R)-2-methyl-1-phenylbut-3-en-1-yl-2-((R)-3-(3,5-dichloro-4-hydroxyphenyl)-2-((2S,3S)-2-((2R,3S)-3-((R,E)-2-methoxy-3-methylhexa-3,5-dien-1-yl)-N,2-dimethyloxirane-2-carboxamido)-3-methylpentanamido)propanamido)-3-hydroxy-3-methylbutanoate (S5)

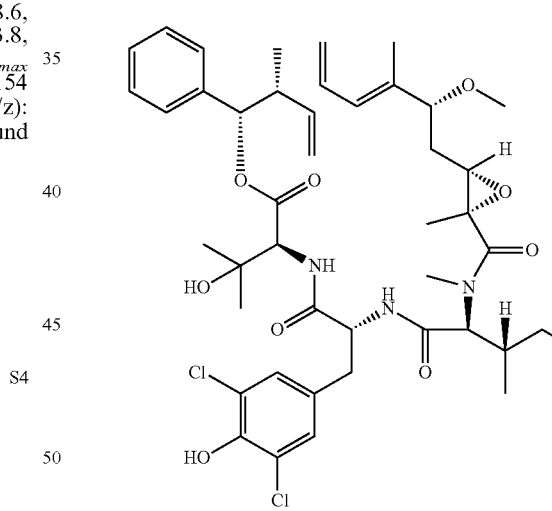

S5

To a solution of 14 (6 mg, 0.027 mmol) in dry DCM (1 mL) was added 1-chloro-N,N,2-trimethyl-1-propenylamine (11 mg, 10 μL, 0.081 mmol) 0° C. The reaction mixture was stirred at room temperature for 5 h before concentrated in vacuo to produce the acyl chloride 31. The acyl chloride 31 was dried under high vacuum for 15 min and used directly for the next step.

To a solution of S4 (12 mg, 0.019 mmol) in dry THF (1 mL) was added DIPEA (26 mg, 0.20 mmol) and the above acyl chloride 31 (dissolved in 1 mL dry DCM) sequentially at −20° C. The reaction mixture was stirred at the same temperature for 10 min before quenched by addition of a saturated aqueous $NH_4Cl$ (0.1 mL). The solvent was removed in vacuo, and the residue was purified by flash column chromatography on silica gel (hexane/ethyl acetate=1/1) to give S5 (11 mg) in 70% yield as a colorless oil. S5: $R_f$=0.35 (hexane/ethyl acetate=1/2). $^1$H NMR (500 MHz, CDCl$_3$): δ 7.34-7.27 (m, 5H), 6.95 (d, J=8.5 Hz, 1H), 6.70 (d, J=8.5 Hz, 1H), 6.62-6.51 (m, 1H), 6.07 (d, J=10.5 Hz, 1H), 5.85 (s, 1H), 5.63 (d, J=10.5 Hz, 1H), 5.61-5.53 (m, 1H), 5.22 (d, J=18.0 Hz, 1H), 5.14 (d, J=10.5 Hz, 1H), 4.99 (d, J=4.5 Hz, 1H), 4.96 (s, 1H), 4.71-4.64 (m, 1H), 4.45 (d, J=8.0 Hz, 1H), 4.31 (d, J=11.0 Hz, 1H), 3.75-3.69 (m, 1H), 3.21-3.11 (m, 5H), 3.04 (s, 3H), 2.90-2.83 (m, 1H), 2.80-2.75 (m, 2H), 2.09-2.03 (m, 1H), 1.88-1.82 (m, 1H), 1.71 (s, 3H), 1.44 (s, 3H), 1.12 (d, J=13.0 Hz, 3H), 1.09 (s, 3H), 1.03 (s, 3H), 0.96-0.88 (m, 1H), 0.85 (t, J=7.5 Hz, 3H), 0.73 (d, J=6.5 Hz, 3H). $^{13}$C NMR (125 MHz, CDCl$_3$): δ 171.9, 170.5, 170.3, 170.0, 146.9, 138.5 (2C), 138.0, 136.6, 132.2, 130.2, 128.9 (2C), 128.8, 128.2, 128.2 (2C), 127.7 (2C), 121.2, 118.0, 116.2, 84.4, 80.8, 71.4, 62.4, 60.4, 60.3, 59.7, 56.1, 54.0, 42.7, 36.1, 33.0, 31.6, 31.2, 29.7, 26.9, 24.7, 15.9, 15.4, 15.0, 11.4, 10.5. IR (film): $v_{max}$ 3315, 2969, 2929, 1737, 1635, 1490, 1380, 1155, 1086 cm$^{-1}$; $[α]^{25}_D$=−32 (c=0.40, MeOH); HR-MS (m/z): [M+Na]$^+$ calcd for C$_{44}$H$_{59}$Cl$_2$N$_3$O$_9$Na$^+$ 866.3521, found 866.3520.

Synthesis of (1R,4S,7R,10S,13S,14R,15E,17E,19R, 21S)-4-((S)-sec-butyl)-7-(3,5-dichloro-4-hydroxybenzyl)-10-(2-hydroxypropan-2-yl)-19-methoxy-1,3, 14,18-tetramethyl-13-phenyl-12,22-dioxa-3,6,9-triazabicyclo[19.1.0]docosa-15,17-diene-2,5,8,11-tetraone (nannocystin A (1))

(1)

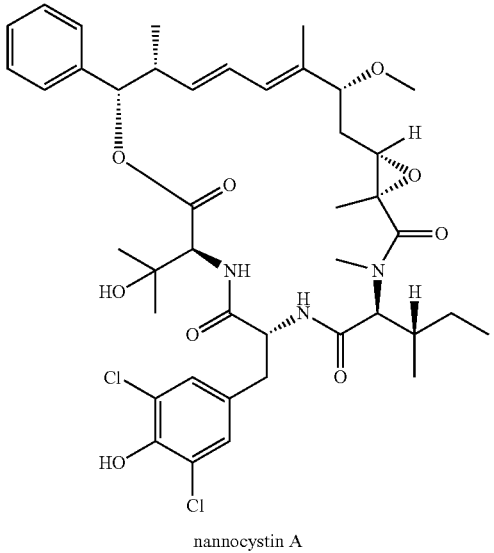

nannocystin A

To a solution of S5 (11 mg, 0.018 mmol) in toluene (110 mL) was added Hoveyda-Grubbs 2$^{nd}$ generation catalyst (1.6 mg, 0.0026 mmol), and the reaction mixture was stirred at 60° C. for 4 h under argon atmosphere. After cooling to 0° C., ethyl vinyl ether (5 mL) was added to the reaction, and stirred for 10 min. The mixture was concentrated in vacuo. The residue was purified through reverse-phase preparative TLC (RP-18 F$_{254S}$) (MeCN/H$_2$O=3/2) to afford 1 (8 mg) in 80% yield as a white solid as a 4:1 mixture. The mixture was separated by semi-preparative HPLC (Gemini 5 u C18 110A column (10.0×150 mm, 5 micron), 55:45 water/acetonitrile, flow rate: 4.0 mL/min). $^1$H NMR (600 MHz, DMSO): δ 9.78 (s, 1H), 8.62 (d, J=10.1 Hz, 1H), 8.06 (d, J=9.6 Hz, 1H), 7.56 (d, J=7.6 Hz, 2H), 7.37 (s, 2H), 7.35-7.29 (m, 2H), 7.25 (t, J=7.3 Hz, 1H), 6.43-6.31 (m, 1H), 6.18 (dd, J=15.3, 4.6 Hz, 1H), 6.12 (d, J=10.8 Hz, 1H), 5.89 (s, 1H), 5.14 (s, 1H), 4.73-4.65 (m, 2H), 4.47 (d, J=11.4 Hz, 1H), 3.62 (dd, J=10.5, 3.3 Hz, 1H), 3.09 (s, 3H), 2.97 (s, 3H), 2.87-2.77 (m, 1H), 2.69-2.56 (m, 2H), 2.16-2.04 (m, 1H), 1.69 (s, 3H), 1.51-1.44 (m, 1H), 1.43 (s, 3H), 1.25-1.18 (m, 2H), 1.14 (s, 3H), 1.03 (s, 3H), 0.96 (d, J=6.8 Hz, 3H), 0.91-0.83 (m, 1H), 0.77 (t, J 7.4 Hz, 3H), 0.33 (d, J=6.6 Hz, 3H). $^{13}$C NMR (150 MHz, DMSO): δ 171.1, 170.9, 169.7, 169.1, 147.7, 140.4, 138.9, 133.8, 131.3 (2C), 130.1 (2C), 129.4 (2C), 128.2, 127.4, 126.4, 125.0, 121.9 (2C), 84.5, 79.3, 72.4, 61.8, 59.6 (2C), 58.5, 55.6, 53.1, 42.3, 37.5, 31.4, 31.0, 30.1, 28.6, 24.8, 24.6, 15.3, 14.9, 11.1, 10.5, 9.9. IR (film): $v_{max}$ 3370, 2971 2925, 2858, 1732, 1659, 1623, 1490, 1470, 1379, 1197, 1153, 1094 cm$^{-1}$; $[α]^{25}_D$=−33 (c=0.07, MeOH); HR-MS (m/z): [M+Na]$^+$ calcd for C$_{42}$H$_{55}$Cl$_2$N$_3$O$_9$Na$^+$838.3208, found 838.3208.

REFERENCES (1) For selected reviews of natural products and drugs, see: (a) Nicolaou, K. C.; Montagnon, T. *Molecules That Changed the World*; Wiley-VCH: Weinheim, Germany, 2008. (b) Dias, D. A.; Urban, S.; Roessner, U. *Metabolites* 2012, 2, 303. (c) Szychowski, J.; Truchon, J.-F.; Bennani, Y L. *J. Med. Chem.* 2014, 57, 9292. (d) Gogineni, V.; Schinazi, R. F.; Hamann, M. T. *Chem. Rev.* 2015, 115, 9655. (e) Mishra, B. B.; Tiwari, V. K. *Eur. J. Med. Chem.* 2011, 46, 4769. (f) Newman, D. J.; Cragg, G. M. *J. Nat. Prod.* 2016, 79, 629.

(2) For reviews of calicheamicins, see: (a) Lee, M. D.; Ellestad, G. A.; Borders, D. B. *Acc. Chem. Res.* 1991, 24, 235. (b) Ellestad, G. A. *Chirality* 2011, 23, 660. (c) Bross, P. F.; Beitz, J.; Chen, G.; Chen, X. H.; Duffy, E.; Kieffer, L.; Roy, S.; Sridhara, R.; Rahman, A.; Williams, G.; Pazdur, R. *Clin. Cancer Res.* 2001, 7, 1490. For reviews of rapamycin, see: (d) Heitman, J.; Movva, N. R.; Hall, M. N. *Science* 1991, 253, 905. (e) Foster, K. G.; Fingar, D. C. *J. Biol. Chem.* 2010, 285, 14071. (f) Easton, J. B.; Houghton, P. J. *Oncogene* 2006, 25, 6436.

(3) Hoffmann, H.; Kogler, H.; Heyse, W.; Matter, H.; Caspers, M.; Schummer, D.; Klemke-Jahn, C.; Bauer, A.; Penarier, G.; Debussche, L.; Bronstrup, M. *Angew. Chem. Int. Ed.* 2015, 54, 10145.

(4) Krastel, P.; Roggo, S.; Schirle, M.; Ross, N. T.; Perruccio, F.; Aspesi, P., Jr.; Aust, T.; Buntin, K.; Estoppey, D.; Liechty, B.; Mapa, F.; Memmert, K.; Miller, H.; Pan, X.; Riedl, R.; Thibaut, C.; Thomas, J.; Wagner, T.; Weber, E.; Xie, X.; Schmitt, E. K.; Hoepfner, D. *Angew. Chem. Int. Ed.* 2015, 54, 10149.

(5) For reviews of EF-1α, see (a) Sasikumar, A. N.; Perez, W. B.; Kinzy, T. G. *WIREs RNA* 2012, 3, 543. (b) Dever, T. E.; Green, R. *Cold Spring Harb Perspect Biol* 2012, 4, a013706.

(6) (a) Pecorari, L.; Marin, O.; Silvestri, C.; Candini, O.; Rossi, E.; Guerzoni, C.; Cattelani, S.; Mariani, S. A.; Corradini, F.; Ferrari-Amorotti, G.; Cortesi, L.; Bussolari, R.; Raschellà, G.; Federico, M. R.; Calabretta, B. *Mol. Cancer* 2009, 8, No. 58. (b) Lamberti, A.; Caraglia, M.; Longo, O.; Marra, M.; Abbruzzese, A.; Arcari, P. *Amino Acids* 2004, 26, 443. (c) Dua, K.; Williams, T. M.; Beretta, L. *Proteomics* 2001, 1, 1191. (d) Lee, J. M. *Reprod. Biol. Endocrinol.* 2003, 1, No. 69.

(7) This work was presented at the 12th SINO-US Chemistry Professors Conference in Guangzhou, China, on Jun. 25, 2016.
(8) For reviews, see: (a) Gradillas, A.; Pérez-Castells, J. Angew. Chem. Int. Ed. 2006, 45, 6086. (b) Nicolaou, K. C.; Bulger, P. G.; Sarlah, D. Angew. Chem. Int. Ed. 2005, 44, 4490. (c) Prunet, J. Eur. J. Org. Chem. 2011, 3634. (d) Hoveyda, A. H.; Zhugralin, A. R. Nature 2007, 450, 243. (e) Fürstner, A. Chem. Commun. 2011, 47, 6505.
(9) Wang, Y; Dai, W.-M. Eur. J. Org. Chem. 2014, 323.
(10) Jain, P.; Antilla, J. C. J. Am. Chem. Soc. 2010, 132, 11884.
(11) (a) Xu, S.; Arimoto, H.; Uemura, D. Angew. Chem. Int. Ed. 2007, 46, 5746. (b) Xu, J.; Caro-Diaz, E. J. E.; Trzoss, L.; Theodorakis, E. A. J. Am. Chem. Soc. 2012, 134, 5072.
(12) Luche, J.-L. J. Am. Chem. Soc. 1978, 100, 2226.
(13) (a) Littke, A. F.; Schwarz, L.; Fu, G. C. J. Am. Chem. Soc. 2002, 124, 6343. (b) Han, X.; Stoltz, B. M.; Corey, E. J. J. Am. Chem. Soc. 1999, 121, 7600.
(14) Gao, Y; Hanson, R. M.; Klunder, J. M.; Ko, S. Y; Masamune, H.; Sharpless, K. B. J. Am. Chem. Soc. 1987, 109, 5765.
(15) (a) Shibuya, M.; Tomizawa M.; Suzuki, I; Iwabuchi, Y J. Am. Chem. Soc. 2006, 128, 8412. (b) Sun, Y; Chen, P.; Zhang, D.; Baunach, M.; Hertweck, C.; Li, A. Angew. Chem. Int. Ed. 2014, 53, 9012. (c) Kuranaga, T.; Sesoko, Y; Sakata, K.; Maeda, N.; Hayata, A.; Inoue, M. J. Am. Chem. Soc. 2013, 135, 5467.
(16) Dettwiler, J. E.; Bélec L.; Lubell, W. D. Can. J. Chem. 2005, 83, 793.
(17) For selected methods of asymmetric synthesis of compound 16, see: (a) Brown, H. C.; Bhat, K. S. J. Am. Chem. Soc. 1986, 108, 5919. (b) Roush, W. R.; Ando, K.; Powers, D. B.; Palkowitz, A. D.; Halterman, R. L. J. Am. Chem. Soc. 1990, 112, 6339. (c) Denmark, S. E.; Fu. J.; Lawler, M. J. J. Org. Chem. 2005, 71, 1523. (d) ref. 9. (e) Kim, H.; Ho, S.; Leighton, J. L. J. Am. Chem. Soc. 2011, 133, 6517. (f) Meng, F.; Jang, H.; Jung, B.; Hoveyda, A. H. Angew. Chem. Int. Ed. 2013, 52, 5046.
(18) For a review of N-methyl amino acid in peptide coupling, see: Humphrey, J. M.; Chamberlin, A. R. Chem. Rev. 1997, 97, 2243.
(19) Devos, A.; Remion, J.; Frisque-Hesbain, A.-M.; Colens, A.; Ghosez, L. J. Chem. Soc., Chem. Commun. 1979, 1180.
(20) For a review of acyl chlorides in peptide coupling, see: Prabhu, G.; Basavaprabhu; Narendra, N.; Vishwanatha, T. M.; Sureshbabu, V. V. Tetrahedron 2015, 71, 2785.
(21) For selected examples of diene-ene RCM, see: (a) Burns, A. R.; McAllister, G. D.; Shanahan, S. E.; Taylor, R. J. K. Angew. Chem. Int. Ed. 2010, 49, 5574. (b) Biswas, K.; Lin, H.; Njardarson, J. T.; Chappell, M. D.; Chou, T.-C.; Guan, Y; Tong, W. P.; He, L.; Horwitz, S. B.; Danishefsky, S. J. J. Am. Chem. Soc. 2002, 124, 9825. (c) Yang, Z.-Q.; Geng, X.; Solit, D.; Pratilas, C. A.; Rosen, N.; Danishefsky, S. J. J. Am. Chem. Soc. 2004, 126, 7881. (d) Lu, K.; Huang, M.; Xiang, Z.; Liu, Y; Chen, J.; Yang, Z. Org. Lett. 2006, 8, 1193. (e) Wang, L.; Gong, J.; Deng, L.; Xiang, Z.; Chen, Z.; Wang, Y; Chen, J.; Yang, Z. Org. Lett. 2009, 11, 1809. (f) Barluenga, S.; Lopez, P.; Moulin, E.; Winssinger, N. Angew. Chem. Int. Ed. 2004, 43, 3467.
(22) For facile dichlorination of tyrosine esters, see: Hayashi, K.; Anzai, N.; Okayasu, I., Endo H. Immunosuppressant Containing O-(5-Amino-2-phenylbenzoxazol-7-yl)methyl-3,5-dichloro-L-tyrosine. Japan Patent JP 5470665 B1, Apr. 16, 2014. In our modified procedure, complete protonation of the amino group by HCl is necessary to avoid side reactions. See Supporting Information.

The invention claimed is:
1. A compound of formula I

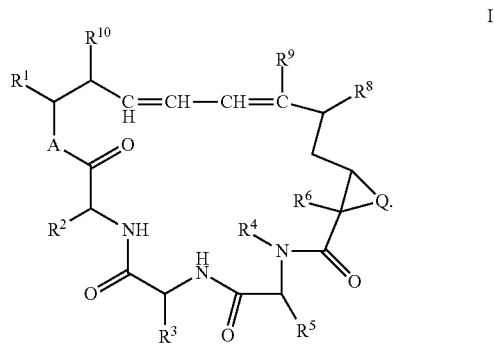

wherein
A is —O— or —NH—;
Q is —$NR^7$—, wherein $R^7$ is hydrogen or ($C_1$-$C_3$)alkyl;
$R^1$ is aryl optionally substituted with one or more substituents chosen independently from —($C_1$-$C_3$)alkyl, halogen, —($C_1$-$C_3$)haloalkyl, —($C_1$-$C_3$)alkyl-OH, and —O($C_1$-$C_3$)alkyl;
$R^2$ is chosen from hydrogen, ($C_1$-$C_{12}$)hydrocarbyl and —($C_1$-$C_{12}$)hydrocarbyl-OH;
$R^3$ is phenyl or benzyl optionally substituted with one or more substituents chosen independently from —($C_1$-$C_3$)alkyl, halogen, —($C_1$-$C_3$)haloalkyl, —($C_1$-$C_3$)alkyl-OH, and —O($C_1$-$C_3$)alkyl;
$R^4$ is hydrogen or ($C_1$-$C_7$)hydrocarbyl;
$R^5$ is hydrogen, ($C_1$-$C_7$)hydrocarbyl or the side chain of a natural amino acid;
$R^6$ is hydrogen or ($C_1$-$C_7$)hydrocarbyl;
$R^8$ is chosen from hydrogen, —($C_1$-$C_3$)alkyl, halogen, hydroxyl, —($C_1$-$C_3$)haloalkyl, —($C_1$-$C_3$)alkyl-OH, and —O($C_1$-$C_3$)alkyl;
$R^9$ is chosen from hydrogen, —($C_1$-$C_3$)alkyl, halogen, hydroxyl, —($C_1$-$C_3$)haloalkyl, —($C_1$-$C_3$)alkyl-OH, —O($C_1$-$C_3$)alkyl, and —C(O)O($C_1$-$C_3$)alkyl; and
$R^{10}$ is chosen from hydrogen, ($C_1$-$C_7$)hydrocarbyl and ($C_1$-$C_7$)oxaalkyl.
2. A compound of claim 1, wherein said compound is an E-alkene.
3. A compound of claim 1, wherein said compound is an Z-alkene.
4. A compound of claim 1, wherein A is NH.
5. A compound of claim 1, wherein A is NH, and $R^1$ is aryl substituted with one or more substituents chosen independently from —($C_1$-$C_3$)alkyl.
6. A compound of claim 1, wherein $R^2$ is hydrogen.
7. A compound of claim 1, wherein the compound is synthetic.
8. A compound of claim 1, wherein A is NH; and
$R^1$ is aryl optionally substituted with one or more substituents chosen independently from —($C_1$-$C_3$)alkyl, halogen, —($C_1$-$C_3$)haloalkyl, —($C_1$-$C_3$)alkyl-OH, and —O($C_1$-$C_3$)alky,
$R^2$ is chosen from hydrogen, ($C_1$-$C_{12}$)hydrocarbyl and —($C_1$-$C_{12}$)hydrocarbyl-OH,
$R^3$ is phenyl or benzyl optionally substituted with one or more substituents chosen independently from —($C_1$-

$C_3$)alkyl, halogen, —($C_1$-$C_3$)haloalkyl, —($C_1$-$C_3$)alkyl-OH, and —O($C_1$-$C_3$)alkyl, $R^4$ is hydrogen or ($C_1$-$C_7$)hydrocarbyl, $R^5$ is hydrogen, ($C_1$-$C_7$)hydrocarbyl or the side chain of a natural amino acid, $R^6$ is hydrogen or ($C_1$-$C_7$)hydrocarbyl, $R^8$ is chosen from hydrogen, —($C_1$-$C_3$)alkyl, halogen, hydroxyl, —($C_1$-$C_3$)haloalkyl, —($C_1$-$C_3$)alkyl-OH, and —O($C_1$-$C_3$)alkyl, $R^9$ is chosen from hydrogen, —($C_1$-$C_3$)alkyl, halogen, hydroxyl, —($C_1$-$C_3$)haloalkyl, —($C_1$-$C_3$)alkyl-OH, —O($C_1$-$C_3$)alkyl, and —C(O)O($C_1$-$C_3$)alkyl, and $R^{10}$ is chosen from hydrogen, ($C_1$-$C_7$)hydrocarbyl and ($C_1$-$C_7$)oxaalkyl.

9. The compound of claim 8, wherein $R^2$ and $R^4$ are hydrogen.

\* \* \* \* \*